US012433532B2

(12) United States Patent
Kubacki et al.

(10) Patent No.: US 12,433,532 B2
(45) Date of Patent: Oct. 7, 2025

(54) FLEXION/EXTENSION SURGICAL GUIDES AND METHODS OF USING THE SAME

(71) Applicant: WRIGHT MEDICAL TECHNOLOGY, INC., Memphis, TN (US)

(72) Inventors: Meghan R. Kubacki, Cookeville, TN (US); Kian-Ming Wong, Lakeland, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 310 days.

(21) Appl. No.: 18/179,488

(22) Filed: Mar. 7, 2023

(65) Prior Publication Data

US 2023/0389860 A1 Dec. 7, 2023

Related U.S. Application Data

(60) Provisional application No. 63/365,717, filed on Jun. 2, 2022.

(51) Int. Cl.
*A61B 5/00* (2006.01)
*A61B 5/107* (2006.01)

(52) U.S. Cl.
CPC .......... *A61B 5/4595* (2013.01); *A61B 5/1071* (2013.01); *A61B 5/6829* (2013.01)

(58) Field of Classification Search
CPC .. A61B 17/15; A61B 17/1682; A61B 17/1775
See application file for complete search history.

(56) References Cited

U.S. PATENT DOCUMENTS 3,839,742 A 10/1974 Link
3,872,519 A 3/1975 Giannestras et al.
3,886,599 A 6/1975 Schlein
3,889,300 A 6/1975 Smith
(Continued)

FOREIGN PATENT DOCUMENTS

CA 2836651 3/2016
CN 101790353 7/2010
(Continued)

OTHER PUBLICATIONS

Search report issued for European patent application No. 13198280 dated Feb. 5, 2014.
(Continued)

*Primary Examiner* — Matthew J Lawson
(74) *Attorney, Agent, or Firm* — Duane Morris LLP

(57) ABSTRACT

A surgical guide includes a body having four sides. The body comprises a first base at the first side, a second base at the second side and an elongated extension between the first and second base. The first base defines at least one first hole and the second base defines at least a second hole. The body is sized and configured to be installed above a joint line of a calcaneus and a talus bone and approximately mid-way along a longitudinal axis of a tibia. The first base is configured to receive at least one dowel of a second surgical guide in the at least one first hole and the second base is configured to receive at least one pin sleeve and pin in the second hole. Systems and methods are also disclosed.

21 Claims, 24 Drawing Sheets

(56) References Cited

U.S. PATENT DOCUMENTS

| | | | |
|---|---|---|---|
| 3,896,502 | A | 7/1975 | Lennox |
| 3,896,503 | A | 7/1975 | Freeman et al. |
| 3,975,778 | A | 8/1976 | Newton, III |
| 3,987,500 | A | 10/1976 | Schlein |
| 4,021,864 | A | 5/1977 | Waugh |
| 4,069,518 | A | 1/1978 | Groth, Jr. et al. |
| 4,156,944 | A | 6/1979 | Schreiber et al. |
| 4,166,292 | A | 9/1979 | Bokros |
| 4,204,284 | A | 5/1980 | Koeneman |
| 4,232,404 | A | 11/1980 | Samuelson et al. |
| 4,309,778 | A | 1/1982 | Buechel et al. |
| 4,470,158 | A | 9/1984 | Pappas et al. |
| 4,755,185 | A | 7/1988 | Tarr |
| 4,968,316 | A | 11/1990 | Hergenroeder |
| 5,041,139 | A | 8/1991 | Brånemark |
| 5,312,412 | A | 5/1994 | Whipple |
| 5,326,365 | A | 7/1994 | Alvine |
| 5,354,300 | A | 10/1994 | Goble et al. |
| 5,395,188 | A | 3/1995 | Bailey et al. |
| 5,423,825 | A | 6/1995 | Levine |
| 5,476,466 | A | 12/1995 | Barrette et al. |
| 5,601,563 | A | 2/1997 | Burke et al. |
| 5,628,749 | A | 5/1997 | Vendrely et al. |
| 5,634,927 | A | 6/1997 | Houston et al. |
| 5,667,511 | A | 9/1997 | Vendrely et al. |
| 5,674,223 | A | 10/1997 | Cipolletti et al. |
| 5,735,904 | A | 4/1998 | Pappas |
| 5,766,259 | A | 6/1998 | Sammarco |
| 5,768,134 | A | 6/1998 | Swaelens et al. |
| 5,776,200 | A | 7/1998 | Johnson et al. |
| 5,817,097 | A | 10/1998 | Howard et al. |
| 5,824,106 | A | 10/1998 | Fournal |
| 5,879,389 | A | 3/1999 | Koshino |
| 5,885,299 | A | 3/1999 | Winslow et al. |
| 5,888,203 | A | 3/1999 | Goldberg |
| 5,897,559 | A | 4/1999 | Masini |
| 5,935,132 | A | 8/1999 | Bettuchi et al. |
| 6,002,859 | A | 12/1999 | DiGioia, III et al. |
| 6,033,405 | A | 3/2000 | Winslow et al. |
| 6,053,922 | A | 4/2000 | Krause et al. |
| 6,102,952 | A | 8/2000 | Koshino |
| 6,183,519 | B1 | 2/2001 | Bonnin et al. |
| 6,245,109 | B1 | 6/2001 | Mendes et al. |
| 6,342,056 | B1 | 1/2002 | Mac-Thiong et al. |
| 6,344,043 | B1 | 2/2002 | Pappas |
| 6,409,767 | B1 | 6/2002 | Pericé et al. |
| 6,436,146 | B1 | 8/2002 | Hassler et al. |
| 6,478,800 | B1 | 11/2002 | Fraser et al. |
| 6,520,964 | B2 | 2/2003 | Tallarida et al. |
| 6,530,930 | B1 | 3/2003 | Marino et al. |
| 6,602,259 | B1 | 8/2003 | Masini |
| 6,610,067 | B2 | 8/2003 | Tallarida et al. |
| 6,610,095 | B1 | 8/2003 | Pope et al. |
| 6,620,168 | B1 | 9/2003 | Lombardo et al. |
| 6,645,215 | B1 | 11/2003 | McGovern et al. |
| 6,663,669 | B1 | 12/2003 | Reiley |
| 6,673,116 | B2 | 1/2004 | Reiley |
| 6,679,917 | B2 | 1/2004 | Ek |
| 6,719,799 | B1 | 4/2004 | Kropf |
| 6,824,567 | B2 | 11/2004 | Tornier et al. |
| 6,852,130 | B2 | 2/2005 | Keller et al. |
| 6,860,902 | B2 | 3/2005 | Reiley |
| 6,863,691 | B2 | 3/2005 | Short et al. |
| 6,875,222 | B2 | 4/2005 | Long et al. |
| 6,875,236 | B2 | 4/2005 | Reiley |
| 6,926,739 | B1 | 8/2005 | O'Connor et al. |
| 6,939,380 | B2 | 9/2005 | Guzman |
| 6,942,670 | B2 | 9/2005 | Heldreth et al. |
| 6,964,663 | B2 | 11/2005 | Grant et al. |
| 7,001,394 | B2 | 2/2006 | Gundlapalli et al. |
| 7,011,687 | B2 | 3/2006 | Deffenbaugh et al. |
| 7,025,790 | B2 | 4/2006 | Parks et al. |
| 7,163,541 | B2 | 1/2007 | Ek |
| 7,238,190 | B2 | 7/2007 | Schon et al. |
| 7,252,684 | B2 | 8/2007 | Dearnaley |
| 7,314,488 | B2 | 1/2008 | Reiley |
| 7,323,012 | B1 | 1/2008 | Stone et al. |
| 7,476,227 | B2 | 1/2009 | Tornier et al. |
| 7,481,814 | B1 | 1/2009 | Metzger |
| 7,485,147 | B2 | 2/2009 | Papps et al. |
| 7,534,246 | B2 | 5/2009 | Reiley et al. |
| 7,534,270 | B2 | 5/2009 | Ball |
| 7,615,082 | B2 | 11/2009 | Naegerl et al. |
| 7,618,421 | B2 | 11/2009 | Axelson, Jr. et al. |
| 7,625,409 | B2 | 12/2009 | Saltzman et al. |
| 7,641,697 | B2 | 1/2010 | Reiley |
| 7,678,151 | B2 | 3/2010 | Ek |
| 7,713,305 | B2 | 5/2010 | Ek |
| 7,717,920 | B2 | 5/2010 | Reiley |
| 7,763,080 | B2 | 7/2010 | Southworth |
| 7,803,158 | B2 | 9/2010 | Hayden |
| 7,850,698 | B2 | 12/2010 | Straszheim-Morley et al. |
| 7,896,883 | B2 | 3/2011 | Ek et al. |
| 7,896,885 | B2 | 3/2011 | Miniaci et al. |
| 7,909,882 | B2 | 3/2011 | Stinnette |
| 7,914,533 | B2 | 3/2011 | Nelson et al. |
| 7,963,996 | B2 | 6/2011 | Saltzman et al. |
| 8,002,841 | B2 | 8/2011 | Hasselman |
| 8,012,217 | B2 | 9/2011 | Strzepa et al. |
| 8,034,114 | B2 | 10/2011 | Reiley |
| 8,034,115 | B2 | 10/2011 | Reiley |
| 8,048,164 | B2 | 11/2011 | Reiley |
| 8,110,006 | B2 | 2/2012 | Reiley |
| 8,114,091 | B2 | 2/2012 | Ratron et al. |
| 8,128,627 | B2 | 3/2012 | Justin et al. |
| 8,167,888 | B2 | 5/2012 | Steffensmeier |
| 8,172,850 | B2 | 5/2012 | McMinn |
| 8,177,841 | B2 | 5/2012 | Ek |
| 8,192,434 | B2 | 6/2012 | Huebner et al. |
| 8,268,007 | B2 | 9/2012 | Barsoum et al. |
| 8,303,667 | B2 | 11/2012 | Younger |
| 8,313,492 | B2 | 11/2012 | Wong et al. |
| 8,317,797 | B2 | 11/2012 | Rasmussen |
| 8,323,346 | B2 | 12/2012 | Tepic |
| 8,337,503 | B2 | 12/2012 | Lian |
| 8,361,159 | B2 | 1/2013 | Ek |
| 8,366,559 | B2 | 2/2013 | Papenfuss et al. |
| 8,430,879 | B2 | 4/2013 | Stoneburner et al. |
| 8,475,463 | B2 | 7/2013 | Lian |
| 8,491,596 | B2 | 7/2013 | Long et al. |
| 8,579,980 | B2 | 11/2013 | DeLurio et al. |
| 8,715,362 | B2 | 5/2014 | Reiley et al. |
| 8,808,297 | B2 | 8/2014 | Stemniski et al. |
| 8,808,303 | B2 | 8/2014 | Stemniski et al. |
| 8,911,444 | B2 | 12/2014 | Bailey |
| 9,220,518 | B2 * | 12/2015 | Neal ...................... A61B 17/15 |
| 9,259,250 | B2 | 2/2016 | Saravia et al. |
| 9,480,571 | B2 | 11/2016 | McGinley et al. |
| 9,492,281 | B2 | 11/2016 | Rouyer et al. |
| 9,566,075 | B2 | 2/2017 | Carroll et al. |
| 9,629,726 | B2 | 4/2017 | Reiley et al. |
| 9,629,730 | B2 | 4/2017 | Reiley |
| 9,675,365 | B2 | 6/2017 | Lancianese et al. |
| 9,907,561 | B2 | 3/2018 | Luna et al. |
| 9,918,724 | B2 | 3/2018 | Luna et al. |
| 10,034,678 | B2 | 7/2018 | Park et al. |
| 10,039,558 | B2 | 8/2018 | Park et al. |
| 10,111,674 | B2 | 10/2018 | Crainich et al. |
| 10,136,904 | B2 | 11/2018 | McGinley et al. |
| 10,149,687 | B2 | 12/2018 | McGinley et al. |
| 10,182,832 | B1 | 1/2019 | Saltzman et al. |
| 10,206,688 | B2 | 2/2019 | Park et al. |
| 10,213,309 | B2 | 2/2019 | Lindsey et al. |
| 10,743,999 | B2 | 8/2020 | Reiley |
| 10,940,012 | B2 | 3/2021 | Sander et al. |
| 11,013,520 | B2 | 5/2021 | Gareiss et al. |
| 11,324,525 | B1 * | 5/2022 | Garvey .............. A61B 17/1775 |
| 12,303,150 | B2 * | 5/2025 | Wong ................. A61B 17/8866 |
| 2002/0068977 | A1 | 6/2002 | Jackson |
| 2002/0082607 | A1 | 6/2002 | Heldreth et al. |
| 2002/0133164 | A1 | 9/2002 | Williamson |
| 2002/0173853 | A1 | 11/2002 | Corl, III et al. |
| 2003/0208280 | A1 | 11/2003 | Tohidi |
| 2003/0236522 | A1 | 12/2003 | Long et al. |

(56) References Cited

U.S. PATENT DOCUMENTS

2004/0030399 A1 2/2004 Asencio
2004/0039394 A1 2/2004 Conti et al.
2004/0068322 A1 4/2004 Ferree
2004/0167631 A1 8/2004 Luchesi et al.
2004/0186585 A1 9/2004 Feiwell
2004/0193268 A1 9/2004 Hazebrouck
2004/0216259 A1 11/2004 Ponziani
2004/0236431 A1 11/2004 Sekel
2005/0004676 A1 1/2005 Schon et al.
2005/0165408 A1 7/2005 Puno et al.
2005/0192674 A1 9/2005 Ferree
2005/0267481 A1 12/2005 Carl et al.
2006/0009857 A1 1/2006 Gibbs et al.
2006/0020345 A1 1/2006 O'Connor et al.
2006/0036257 A1 2/2006 Steffensmeier et al.
2006/0116679 A1 6/2006 Lutz et al.
2006/0142870 A1 6/2006 Robinson et al.
2006/0229730 A1 10/2006 Reiley et al.
2006/0235541 A1 10/2006 Hodorek
2006/0247788 A1 11/2006 Ross
2007/0038303 A1 2/2007 Myerson et al.
2007/0100346 A1 5/2007 Wyss et al.
2007/0112431 A1 5/2007 Kofoed
2007/0162025 A1 7/2007 Tornier et al.
2007/0173944 A1 7/2007 Keller et al.
2007/0173947 A1 7/2007 Ratron
2007/0213830 A1 9/2007 Ammann et al.
2007/0233129 A1 10/2007 Bertagnoli et al.
2007/0276400 A1 11/2007 Moore et al.
2007/0288030 A1 12/2007 Metzger et al.
2008/0015602 A1 1/2008 Axelson
2008/0097617 A1 4/2008 Fellinger et al.
2008/0103603 A1 5/2008 Hintermann
2008/0109081 A1 5/2008 Bao et al.
2008/0195233 A1 8/2008 Ferrari et al.
2008/0215156 A1 9/2008 Duggal et al.
2008/0287954 A1 11/2008 Kunz et al.
2008/0312745 A1 12/2008 Keller et al.
2009/0024131 A1 1/2009 Metzger et al.
2009/0043309 A1 2/2009 Rasmussen
2009/0043310 A1 2/2009 Rasmussen
2009/0054992 A1 2/2009 Landes et al.
2009/0082875 A1 3/2009 Long
2009/0105767 A1 4/2009 Reiley
2009/0105840 A1 4/2009 Reiley
2009/0182433 A1 7/2009 Reiley et al.
2009/0198341 A1 8/2009 Choi et al.
2009/0234360 A1 9/2009 Alexander
2009/0276052 A1 11/2009 Regala et al.
2010/0010493 A1 1/2010 Dower
2010/0023066 A1 1/2010 Long et al.
2010/0023126 A1 1/2010 Grotz
2010/0042215 A1 2/2010 Stalcup et al.
2010/0057216 A1 3/2010 Gannoe et al.
2010/0069910 A1 3/2010 Hasselman
2010/0198355 A1 8/2010 Kofoed et al.
2010/0212138 A1 8/2010 Carroll et al.
2010/0241237 A1 9/2010 Pappas
2010/0256773 A1 10/2010 Thijs et al.
2010/0262150 A1 10/2010 Lian
2010/0305572 A1 12/2010 Saltzman et al.
2010/0318088 A1 12/2010 Warne et al.
2010/0331984 A1 12/2010 Barsoum et al.
2011/0029090 A1 2/2011 Zannis et al.
2011/0035018 A1 2/2011 Deffenbaugh et al.
2011/0035019 A1 2/2011 Goswami et al.
2011/0071645 A1 3/2011 Bojarski et al.
2011/0106268 A1 5/2011 Deffenbaugh et al.
2011/0112542 A1 5/2011 Gross
2011/0125200 A1 5/2011 Hanson et al.
2011/0125275 A1 5/2011 Lipman et al.
2011/0125284 A1 5/2011 Gabbrielli et al.
2011/0152868 A1 6/2011 Kourtis et al.
2011/0152869 A1 6/2011 Ek et al.
2011/0166608 A1 7/2011 Duggal et al.
2011/0190829 A1 8/2011 Duggal et al.
2011/0218542 A1 9/2011 Lian
2011/0245835 A1 10/2011 Dodd et al.
2011/0253151 A1 10/2011 Tochigi et al.
2011/0276052 A1 11/2011 Hasselman
2011/0295380 A1 12/2011 Long
2012/0010718 A1 1/2012 Still
2012/0046753 A1 2/2012 Cook et al.
2012/0053591 A1 3/2012 Haines et al.
2012/0053644 A1 3/2012 Landry et al.
2012/0083789 A1 4/2012 Blakemore et al.
2012/0109131 A1 5/2012 Vasarhelyi et al.
2012/0109326 A1 5/2012 Perler
2012/0130376 A1* 5/2012 Loring .................. A61B 17/15 606/90
2012/0136443 A1 5/2012 Wenzel
2012/0185057 A1 7/2012 Abidi et al.
2012/0191210 A1 7/2012 Ratron et al.
2012/0239045 A1 9/2012 Li
2012/0245701 A1 9/2012 Zak et al.
2012/0271314 A1 10/2012 Stemniski et al.
2012/0271430 A1 10/2012 Arnett et al.
2012/0277745 A1* 11/2012 Lizee ................ A61B 17/1739 606/59
2013/0041473 A1 2/2013 Rouyer et al.
2013/0116797 A1 5/2013 Coulange et al.
2013/0190766 A1* 7/2013 Harris .................... A61B 17/15 606/87
2014/0020690 A1 1/2014 Triplett
2014/0039565 A1 2/2014 Martineau et al.
2014/0163570 A1 6/2014 Reynolds et al.
2014/0236157 A1 8/2014 Tochigi et al.
2014/0276853 A1 9/2014 Long et al.
2014/0296995 A1 10/2014 Reiley et al.
2014/0309640 A1 10/2014 Smith et al.
2014/0336658 A1* 11/2014 Luna ...................... A61B 17/15 606/87
2015/0045801 A1 2/2015 Axelson et al.
2015/0157467 A1* 6/2015 McGinley .......... A61B 17/1739 606/86 R
2015/0257900 A1 9/2015 Dees, Jr.
2016/0135815 A1 5/2016 Loring et al.
2016/0135857 A1 5/2016 Marrero, Sr.
2016/0256293 A1* 9/2016 Mauldin ............... A61F 2/4606
2016/0361071 A1 12/2016 Mahfouz
2016/0367371 A1 12/2016 De Beaubien et al.
2017/0189198 A1 7/2017 Reiley et al.
2018/0177511 A1 6/2018 Luna et al.
2018/0177513 A1 6/2018 Stemniski et al.
2018/0263639 A1 9/2018 McGinley et al.
2019/0059917 A1 2/2019 Saltzman
2019/0059918 A1 2/2019 Saltzman et al.
2019/0076261 A1 3/2019 Mutchler et al.
2019/0133612 A1 5/2019 McGinley
2019/0150957 A1 5/2019 Wilkinson
2019/0350717 A1 11/2019 Tuttle
2020/0046374 A1 2/2020 Luttrell et al.
2020/0060690 A1* 2/2020 Woodard ............. A61B 17/157
2020/0297353 A1 9/2020 Bomar et al.
2021/0059769 A1* 3/2021 Barmes .............. A61B 17/1764
2021/0077276 A1* 3/2021 Garvey ................. A61F 2/4606
2021/0298771 A1* 9/2021 Lee ........................ A61B 17/15
2021/0298911 A1* 9/2021 Dalton ............... A61B 17/1775
2022/0316504 A1 10/2022 Kubacki
2023/0263535 A1* 8/2023 Hyer .................. A61B 17/1775 606/82
2023/0346395 A1* 11/2023 Kubacki ............... A61F 2/4606
2025/0195239 A1* 6/2025 Luna .................. A61B 17/1682

FOREIGN PATENT DOCUMENTS

EP 2967697 4/2018
EP 3354233 10/2019
GB 2480846 12/2011
JP H11-500035 1/1999
JP 2006150055 6/2006
JP 2007508123 4/2007
JP 2007518453 7/2007

(56) References Cited

FOREIGN PATENT DOCUMENTS

| | | | |
|---|---|---|---|
| JP | 2007519477 | 7/2007 | |
| JP | 2007536011 | 12/2007 | |
| JP | 2009148597 | 7/2009 | |
| JP | 2011526189 | 10/2011 | |
| JP | 2012518517 | 8/2012 | |
| JP | 2013500810 | 1/2013 | |
| JP | 2013511358 | 4/2013 | |
| JP | 5412334 | 2/2014 | |
| JP | 2014131738 | 7/2014 | |
| WO | WO 9625106 | 8/1996 | |
| WO | WO 0166021 A1 | 9/2001 | |
| WO | WO 2005011523 A2 | 2/2005 | |
| WO | WO 2005037135 | 4/2005 | |
| WO | WO 2006022923 | 3/2006 | |
| WO | WO 2006023824 | 3/2006 | |
| WO | WO 2006099270 | 9/2006 | |
| WO | WO 2007084846 | 7/2007 | |
| WO | WO 2009143374 | 11/2009 | |
| WO | WO 2009158522 | 12/2009 | |
| WO | WO 2010099142 | 9/2010 | |
| WO | WO 2010135156 | 11/2010 | |
| WO | WO 2011015863 | 2/2011 | |
| WO | WO 2011063281 | 5/2011 | |
| WO | WO 2011151657 | 12/2011 | |
| WO | WO 2012088036 | 6/2012 | |
| WO | WO 2012116089 | 8/2012 | |
| WO | WO 2012158917 | 11/2012 | |
| WO | WO 2013169475 | 11/2013 | |
| WO | WO 2014152535 | 9/2014 | |
| WO | WO 2015167581 | 11/2015 | |
| WO | WO 2016181168 | 11/2015 | |
| WO | WO 2016005722 | 1/2016 | |
| WO | WO 2016039762 | 3/2016 | |
| WO | WO-2020124055 A1 * | 6/2020 | ............. A61B 17/15 |

OTHER PUBLICATIONS

International Search Report for International patent application No. PCT/US2014/027448 dated Jul. 7, 2014.

International Preliminary Report on Patentability issued for International patent application No. PCT/US2014/027448, Sep. 15, 2015, 8 pages.

Partial European Search Report issued in connection with European patent application No. 14768333.8, Oct. 26, 2016, 6 pages.

Patent Examination Report No. 1 issued in connection with Australian patent application No. 2015202080, Jul. 5, 2016, 4 pages.

First Office Action issued for Japanese patent application No. 2016-117842, Sep. 12, 2017, 5 pages.

First Office Action issued in connection with corresponding Japanese Patent Application No. 2020-016447, Apr. 6, 2021, 4 pages.

Office Action in corresponding Canadian Patent Application No. 2,904,652, Jun. 2, 2020, 6 pages.

First Examination Report issued in corresponding Australian Patent Application No. 2019213412, Sep. 3, 2020, 5 pages.

First Office Action in corresponding Canadian Patent Application No. 2,904,652, Jan. 28, 2020, 5 pages.

Final Office Action issued in connection with corresponding Japanese Patent Application No. 206-502443, May 15, 2018, 3 pages.

Extended European Search Report issued in connection with corresponding European Patent Application No. 18160378.8, Jun. 29, 2018, 7 pages.

Second Office Action issued in connection with corresponding Chinese Patent Application No. 2018071101785100, dated Jul. 16, 2016, 6 pages.

First Office Action in corresponding Japanese Patent Application No. 2018-178853, Sep. 3, 2018, 3 pages.

Examination Report No. 1 issued in connection with corresponding Australian Patent Application No. 20182000073, Dec. 24, 2018, 3 pages.

First Office Action issued in connection with corresponding Japanese Patent Application No. 2018-092289, Mar. 5, 2019, 2 pages.

Extended European Search Report and Opinion in connection with European Patent Application No. 14768333.8, dated Jan. 30, 2017, 10 pages.

First Office Action issued in connection with Chinese Patent Application No. 2017800899442 dated Apr. 6, 2022, 8 pages.

International Search Report and Written Opinion issued in connection with International Patent Application No. PCT/US2021/025873, Sep. 2, 2021.

Orthopedic Designs North America, Inc., http://odi-na.com/?service=talon-distalfix-fermoral-nail-system, accessed via Internet, Jul. 22, 2022.

Arthrex, "Arthrex—Intramedullary Nails," https://ww.arthrex.com/foot-ankle/intramedullary-nails, accessed via Internet, Jul. 22, 2022.

Inbone II Total Ankle Surgical Technique, Wright Medical Technology, Inc., Mar. 12, 2014, 64 pages.

Infinity Total Ankle System Surgical Technique, Wright Medical Techology, Inc., Aug. 8, 2015, 76 pages.

First Examination Report issued in connection with Australian Patent Application No. 2020277219, Nov. 19, 2021, 7 pages.

International Search Report and Written Opinion issued in connection with International Patent Application No. PCT/US2016/023729, Feb. 14, 2017, 14 pages.

First Examination Report issued in connection with Australian Patent Application No. 2019246766, Apr. 17, 2020, 9 pages.

Supplementary European Search Report issued in connection with corresponding European Patent Application No. 16895669.6 Oct. 21, 2019, 6 pages.

Office Action in connection with corresponding Canadian Patent Application No. 3,014,284, Jun. 17, 2019, 4 pages.

First Examination issued in connection with Australian Patent Application No. 2016398429, Jan. 21, 2019, 4 pages.

International Search Report and Written Opinion issued in connection with International Patent Application No. PCT/US2021/071308, Dec. 27, 2021, 10 pages.

Prophecy Inbone Preoperative Navigation Guides Surgical Technique, Wright Medical Technology, Inc., 64 pages.

Sidekick Coretrak Tube Fixator, Wright Medical Technology, Inc., 8 pages.

Extended European Search Report issued in connection with European Patent Application No. 22185245.2, Nov. 28, 2022, 9 pages.

International Search Report and Written Opinion issued in connection with International Patent Application No. PCT/US2021/057014, Mar. 17, 2022, 19 pages.

* cited by examiner

FLEXION/EXTENSION SURGICAL GUIDES AND METHODS OF USING THE SAME

CROSS-REFERENCE TO RELATED APPLICATION

This application claims priority under 35 U.S.C. § 119(e) to U.S. Provisional Application No. 63/365,717, filed on Jun. 2, 2022, the entire contents of which are incorporated herein by reference.

INCORPORATION BY REFERENCE

The disclosures of U.S. Pat. Nos. 9,918,724 and 10,136,904 are incorporated by reference herein in their entireties.

FIELD OF DISCLOSURE

The disclosed apparatuses, systems, and methods relate to surgical tools. More specifically, the disclosed apparatuses, systems, and methods relate to surgical tools for determining the flexion and/or extension angle when performing ankle surgery, including total ankle surgery.

BACKGROUND

The ankle is a joint that is often compared to a hinge. This joint is made from the combination of three bones—the tibia, fibula and talus. The talus is the ankle bone. The upper portion of the talus fits inside a socket that is formed by the lower portion of the leg, which includes the tibia and the fibula. Ankle joint deterioration can develop from arthritis, bone degeneration, and/or injury, which may result in pain, lower range of motion, and decreased quality of life. To treat these conditions, physicians often recommend ankle replacement surgery with an implant. One example of such an implant is the INFINITY™ Total Ankle System available from Stryker Corp., of Kalamazoo, MI, although one of ordinary skill in the art will understand that the disclosure is not limited to such implants. The process of implanting an ankle replacement system typically includes the use of guides for determining the proper placement and angle of the implant, among other surgical guides and tools.

SUMMARY

The disclosed guides, systems, and methods reduce the number of surgical components and simplify the manner in which a surgeon determines the flexion and/or extension angle of an ankle implant, as compared to conventional instrumentation. The disclosed guides, systems, and methods result in a more streamlined and efficient method for determining the proper placement and angle of an ankle implant. Additionally, the disclosed guides, systems, and methods are smaller in size, which allows for improved manipulation of the guides during surgery. Further, the disclosed guides, systems, and methods provide enhanced visibility cues which allow for greater accuracy in placement of the guides and ankle implant during surgery.

In some embodiments, the disclosed surgical guide includes a first side, a second side, a third side, and a fourth side, with the third and fourth sides extending between the first and second sides. The body comprises a first base at the first side, a second base at the second side and an elongated extension between the first and second base. The first base defines at least one first hole and the second base defines at least a second hole. The body is sized and configured to be installed above a joint line of a calcaneus and a talus bone and approximately mid-way along a longitudinal axis of a tibia. The first base is configured to receive at least one dowel of a second surgical guide in the at least one first hole and the second base is configured to receive at least one pin sleeve and pin in the second hole.

In some embodiments, the first base includes a posterior side comprising a protrusion configured to engage a channel of a third surgical guide.

In some embodiments, the first base includes a posterior side comprising a channel configured to engage a side of a third surgical guide.

In some embodiments, the first base includes an anterior side comprising an adjustment mechanism to lock the third surgical guide and the surgical guide.

In some embodiments, the first and second base are rectangular in shape.

In some embodiments, the first base is configured to receive at least one pin in the at least one first hole.

In some embodiments, the second base includes a superior side and an inferior side, as well as an engagement portion disposed within a channel configured to allow movement of the engagement portion between the superior side and inferior side. The engagement portion defines at least the second hole configured to receive the at least one pin sleeve and pin.

In some embodiments, the second base includes an adjustment mechanism to lock the engagement portion in place.

In some embodiments, the engagement portion is rectangular in shape.

In some embodiments, the engagement portion includes an adjustment mechanism configured to lock a pin in place.

In some embodiments, the pin sleeve includes at least one slot configured to engage a portion of the adjustment mechanism configured to lock a pin in place.

In some embodiments, the pin sleeve comprises two slots, in which one slot is located on the superior side of the pin sleeve and one slot is located on the inferior side of the pin sleeve. Each slot is configured to engage a portion of the adjustment mechanism configured to lock a pin in place in either configuration of the pin sleeve.

In some embodiments, the pin sleeve is rectangular in shape and the second hole is similarly configured to receive the rectangular shape of the pin sleeve.

In some embodiments, at least a portion of the body is formed from radiopaque material.

In some embodiments, the disclosed system comprises a first guide including a body having a first side, a second side, a third side, and a fourth side, with the third and fourth sides extending between the first and second sides. The body includes a first base at the first side, a second base at the second side and an elongated extension between the first and second base. The first base defines at least one first hole and the second base defines at least a second hole. The body is sized and configured to be installed above a joint line of a calcaneus and a talus bone and approximately mid-way along the longitudinal axis of a tibia. The first base is configured to receive at least one protrusion of a second surgical guide in the at least one first hole and the second base is configured to receive at least one pin sleeve and pin in the second hole.

In some embodiments, the disclosed system includes a second guide having a transverse beam that extends between a first arm and a second arm. The second guide is configured to be coupled to the first guide.

In some embodiments, first and second protrusions extend from the transverse beam of the second guide. The first and second protrusions are sized and configured to be received in the at least one first hole defined by the first base for coupling the second guide to the first guide.

In some embodiments, each of the first and second arms of the second guide define at least one of a hole or a slot for receiving an elongate radiopaque device therein.

In some embodiments, the disclosed system includes a third guide having a first portion extending longitudinally in a first direction and a second portion extending laterally from the first portion in a second direction. The first portion defines a first channel that runs the length of first portion on a first side and defines a second channel on a second side, which is disposed opposite the first side.

In some embodiments, the second portion of the third guide defines a guide hole which is configured to engage a shaft of a fourth surgical guide inserted above a joint line of a calcaneus and a talus bone.

In some embodiments, the first base of the first guide includes a posterior side comprising a protrusion configured to engage a channel of the third guide.

In some embodiments, the first base of the first guide includes a posterior side comprising a channel configured to engage a side of the third surgical guide.

In some embodiments, the first base of the first guide includes an anterior side comprising an adjustment mechanism to align the third guide and the first guide.

In some embodiments, the disclosed method includes: inserting a first guide above a joint line of a calcaneus and a talus bone; connecting a second guide to the first guide, the second guide having a first portion extending longitudinally in a first direction and a second portion extending laterally from the first portion in a second direction, wherein the first portion defines a first channel that runs the length of first portion on a first side and defines a second channel on a second side, which is disposed opposite the first side, and the second portion of the second guide defines a guide hole which is configured to engage a shaft of the first guide; connecting a portion of the second guide to a third guide, the third guide including a body having a first side, a second side, a third side, and a fourth side, the third and fourth sides extending between the first and second sides, wherein the body comprises a first base at said first side, a second base at said second side and an elongated extension between the first and second base, wherein the first base defines at least one first hole and the second base defines at least a second hole, and wherein the body is sized and configured to be installed above a joint line of a calcaneus and a talus bone and approximately mid-way along the longitudinal axis of a tibia; locking the location of the second guide and third guide about an axis defined by a shaft of the tibia using an adjustment mechanism attached to the third guide; coupling a fourth guide to the third guide, the fourth guide including first and second arms that are coupled together by a transverse beam and each of the first and second arms of the fourth guide define at least one of a hole or a slot for receiving an elongate radiopaque device therein; coupling an elongate radiopaque device to the fourth guide through the at least one hole or slot of the fourth guide; determining the alignment of the fourth guide and elongate radiopaque device using fluoroscopy; inserting at least one pin sleeve and pin into the second hole of the third guide; removing the fourth guide and elongate radiopaque device; inserting pins into the at least one first hole of the third guide and through two cortices of the tibia; and removing the first, second and third guides.

In some embodiments, coupling the fourth guide to the third guide includes inserting at least one protrusion extending from the transverse beam of the fourth guide into at least one hole defined by the third guide.

In some embodiments, inserting at least one pin into the second hole of the third guide further includes turning an adjustment mechanism located on the second base to lock the pin in place after inserting the pin sleeve and pin into the second hole of the third guide.

In some embodiments, the disclosed method includes loosening all adjustment mechanisms attached to the third guide prior to removing the first, second and third guides.

In some embodiments, the disclosed method includes: inserting a first guide above a joint line of a calcaneus and a talus bone; connecting a portion of a second guide to a third guide, the second guide having a first portion extending longitudinally in a first direction and a second portion extending laterally from the first portion in a second direction, wherein the first portion defines a first channel that runs the length of first portion on a first side and defines a second channel on a second side, which is disposed opposite the first side, and the second portion of the second guide defines a guide hole which is configured to engage a shaft of the first guide, wherein the third guide includes a body having a first side, a second side, a third side, and a fourth side, the third and fourth sides extending between the first and second sides, wherein the body comprises a first base at said first side, a second base at said second side and an elongated extension between the first and second base, wherein the first base defines at least one first hole and the second base defines at least a second hole, and wherein the body is sized and configured to be installed above a joint line of a calcaneus and a talus bone and approximately mid-way along the longitudinal axis of a tibia; inserting at least one pin sleeve into the second hole of the third guide; coupling a fourth guide to the third guide, the fourth guide including first and second arms that are coupled together by a transverse beam and each of the first and second arms of the fourth guide define at least one of a hole or a slot for receiving an elongate radiopaque device therein; coupling an elongate radiopaque device to the fourth guide through the at least one hole or slot of the fourth guide; connecting the second guide to the first guide; locking the location of the second guide and third guide about an axis defined by a shaft of the tibia using an adjustment mechanism attached to the third guide; determining the alignment of the fourth guide and elongate radiopaque device using fluoroscopy; inserting at least one pin into the pin sleeve that is inserted into the second hole of the third guide; removing the fourth guide and elongate radiopaque device; inserting pins into the at least one first hole of the third guide and through two cortices of the tibia; and removing the first, second and third guides.

BRIEF DESCRIPTION OF THE DRAWINGS

The features and advantages of the present disclosures will be more fully disclosed in, or rendered obvious by the following detailed descriptions of example embodiments. The detailed descriptions of the example embodiments are to be considered together with the accompanying drawings wherein like numbers refer to like parts and further wherein.

DETAILED DESCRIPTION

Figure 1:
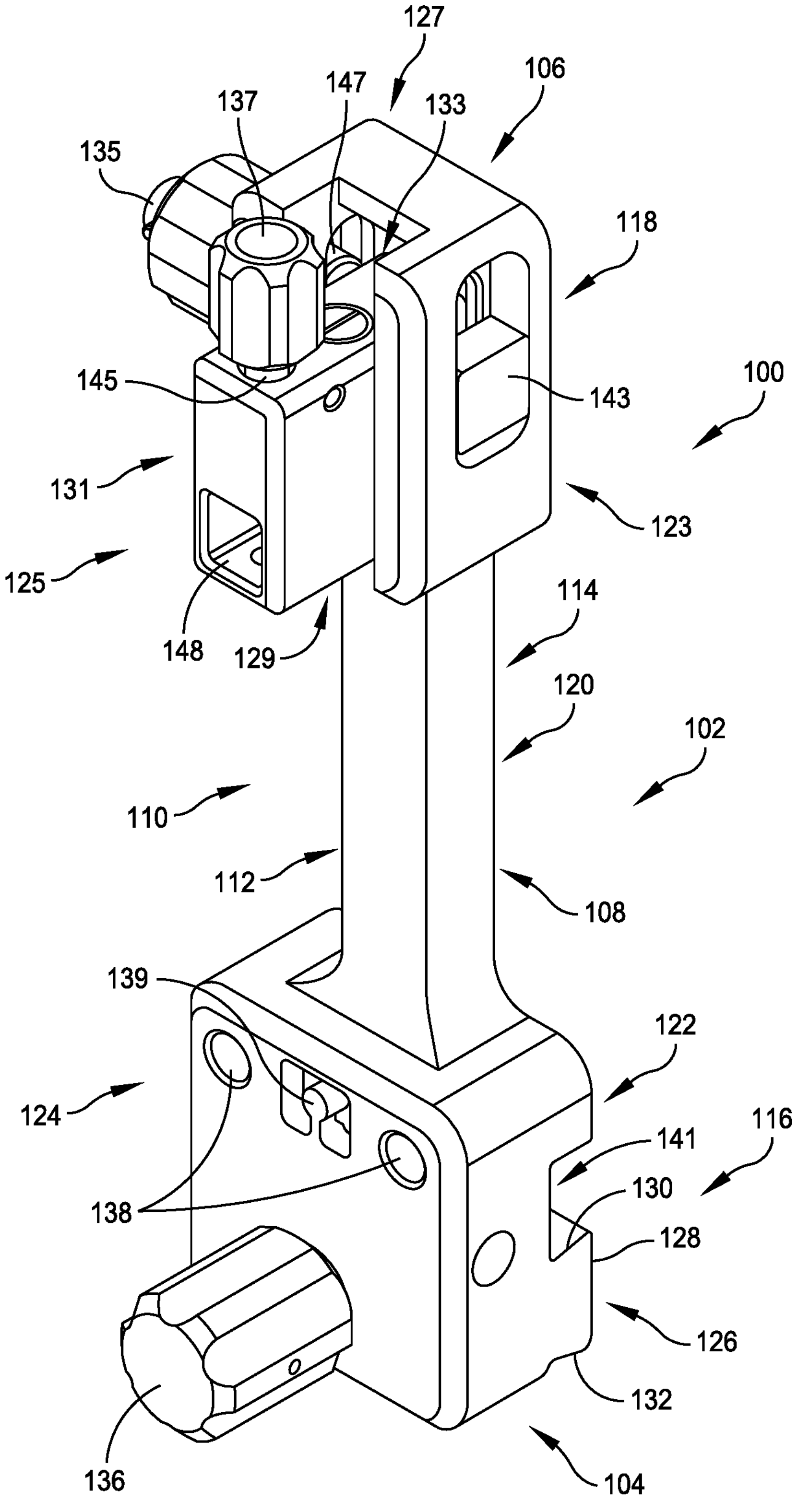
FIG. 1 is an isometric perspective view of one example of a guide in accordance with some embodiments.

This description of the exemplary embodiments is to be read in connection with the accompanying drawings, which are to be considered part of the entire written description. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

The disclosed guides reduce the number of components and provides a simpler manner of determining the flexion and/or extension angle of an ankle implant compared to conventional instrumentation, which yields a more streamlined and efficient method. The disclosed guides also have a reduced size, which improves the ability of the surgeon to manipulate the guides during surgery. Further, the disclosed guides include enhanced visibility cues for accurate placement during the surgery.

Figure 2:
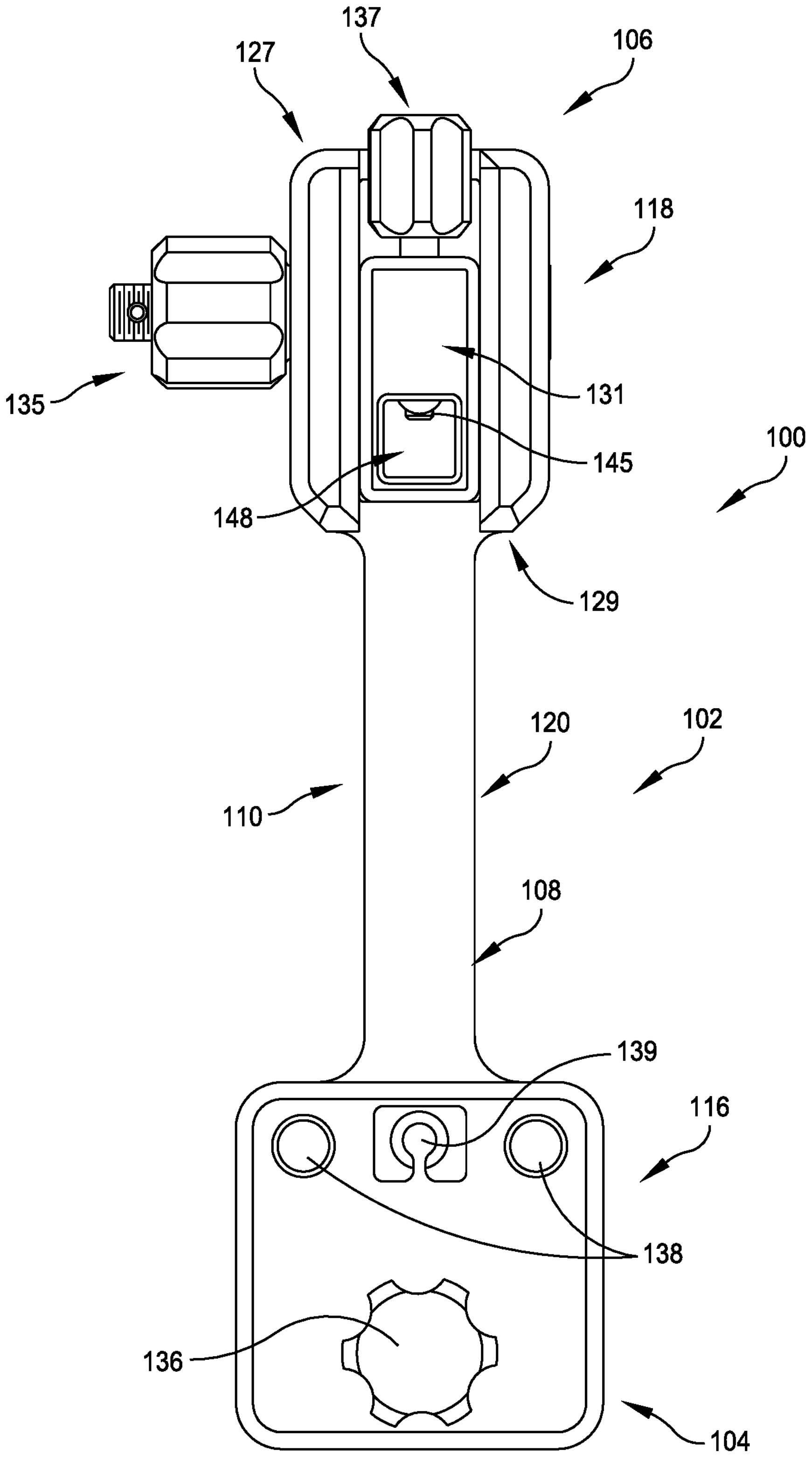
FIG. 2 is a front or anterior side view of the guide illustrated in FIG. 1 in accordance with some embodiments.
Figure 3:
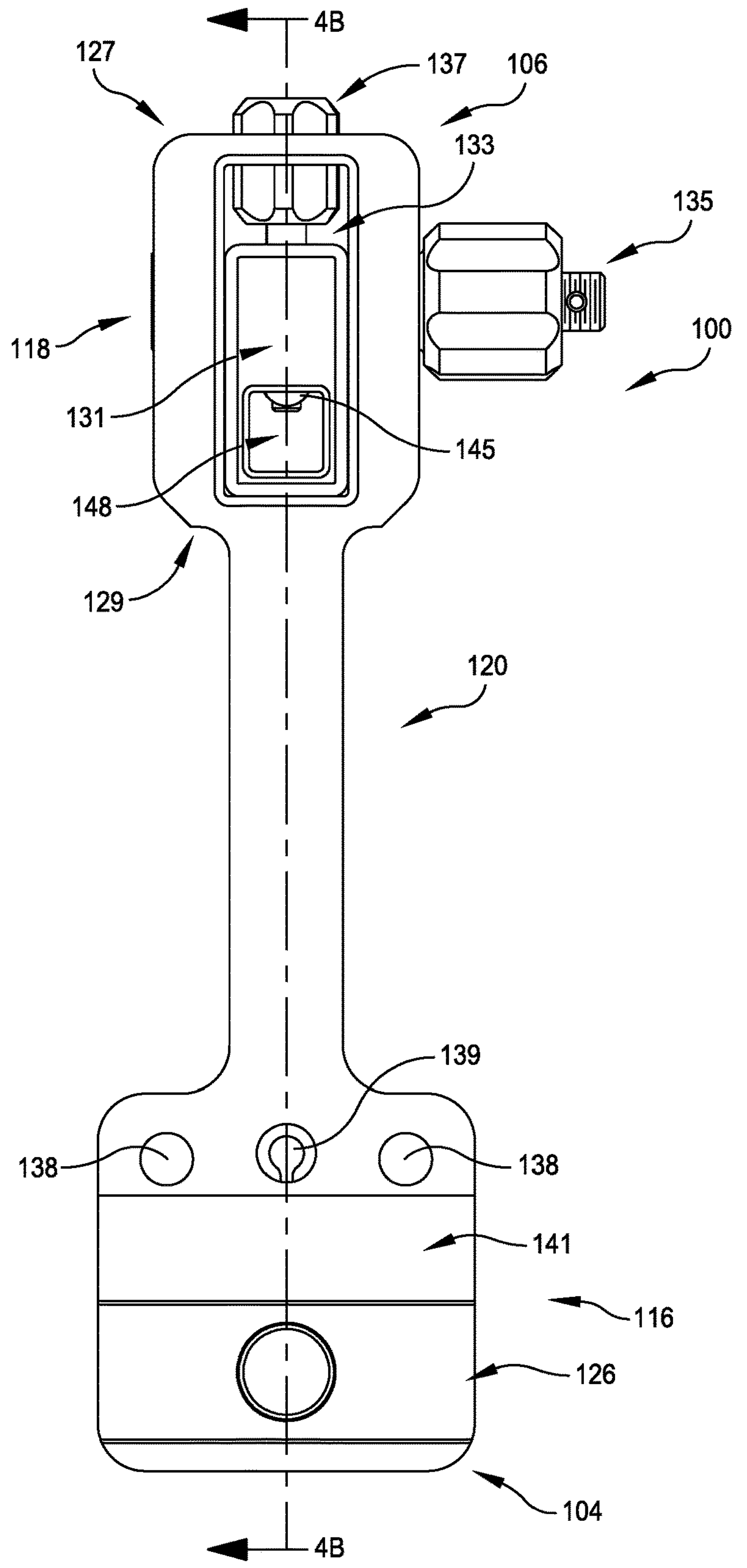
FIG. 3 is a rear or posterior side view of the guide illustrated in FIG. 1 in accordance with some embodiments.
Figure 4A:
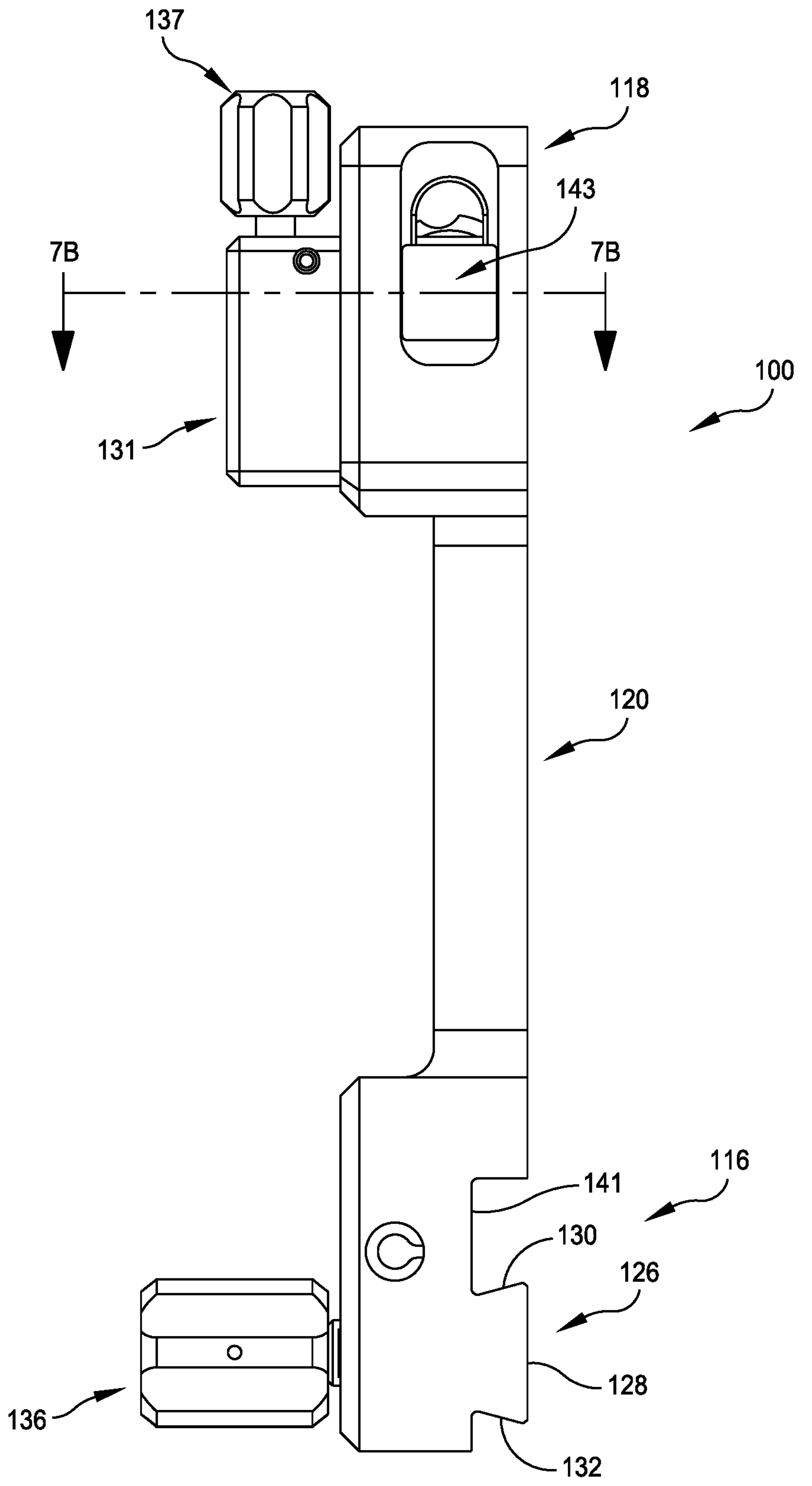
FIG. 4A is a side view of the guide illustrated in FIG. 1 in accordance with some embodiments.
Figure 4B:
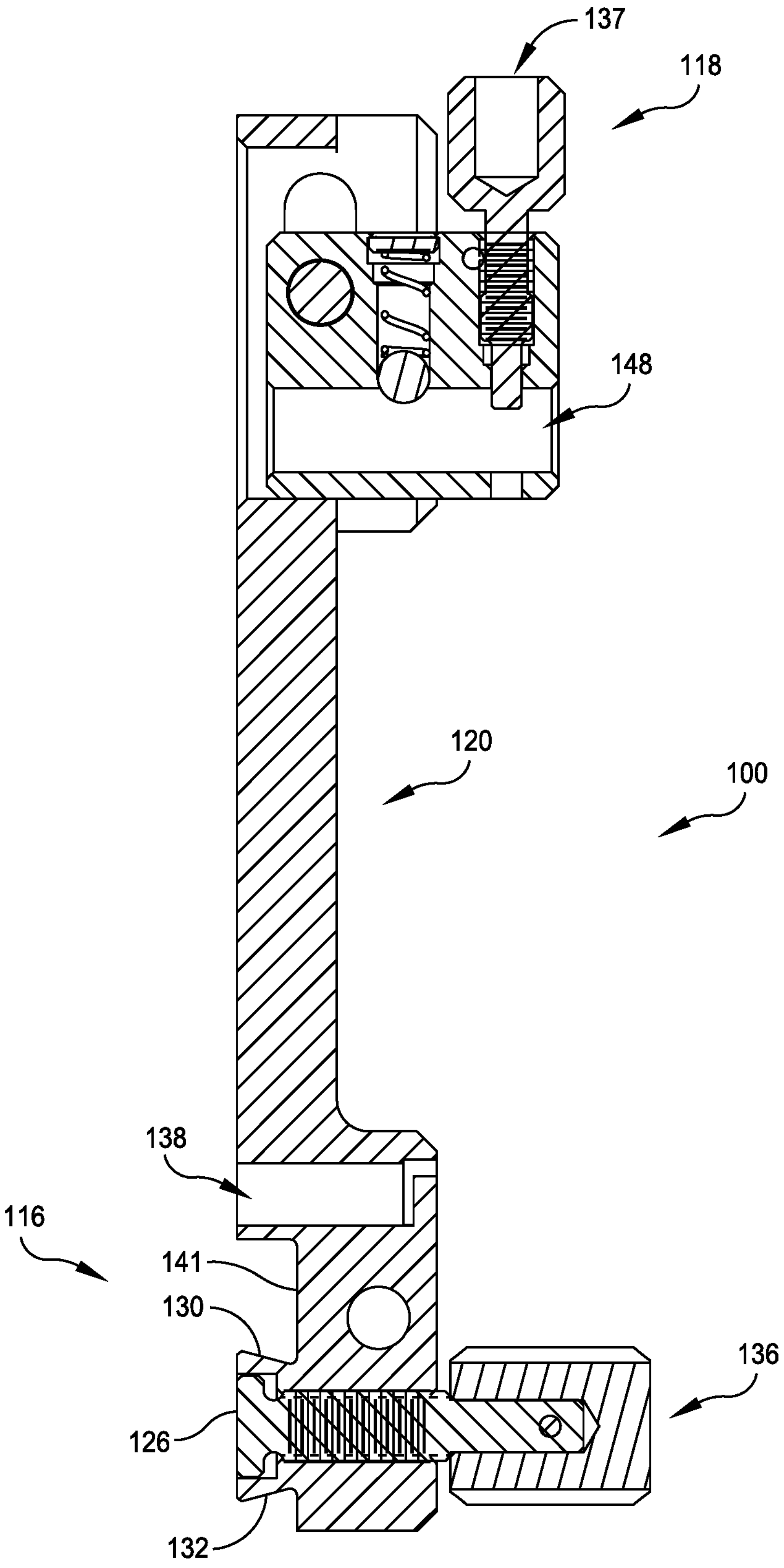
FIG. 4B is a cross-sectional view of guide 100 taken along its vertical axis, in accordance with some embodiments.
Figure 5:
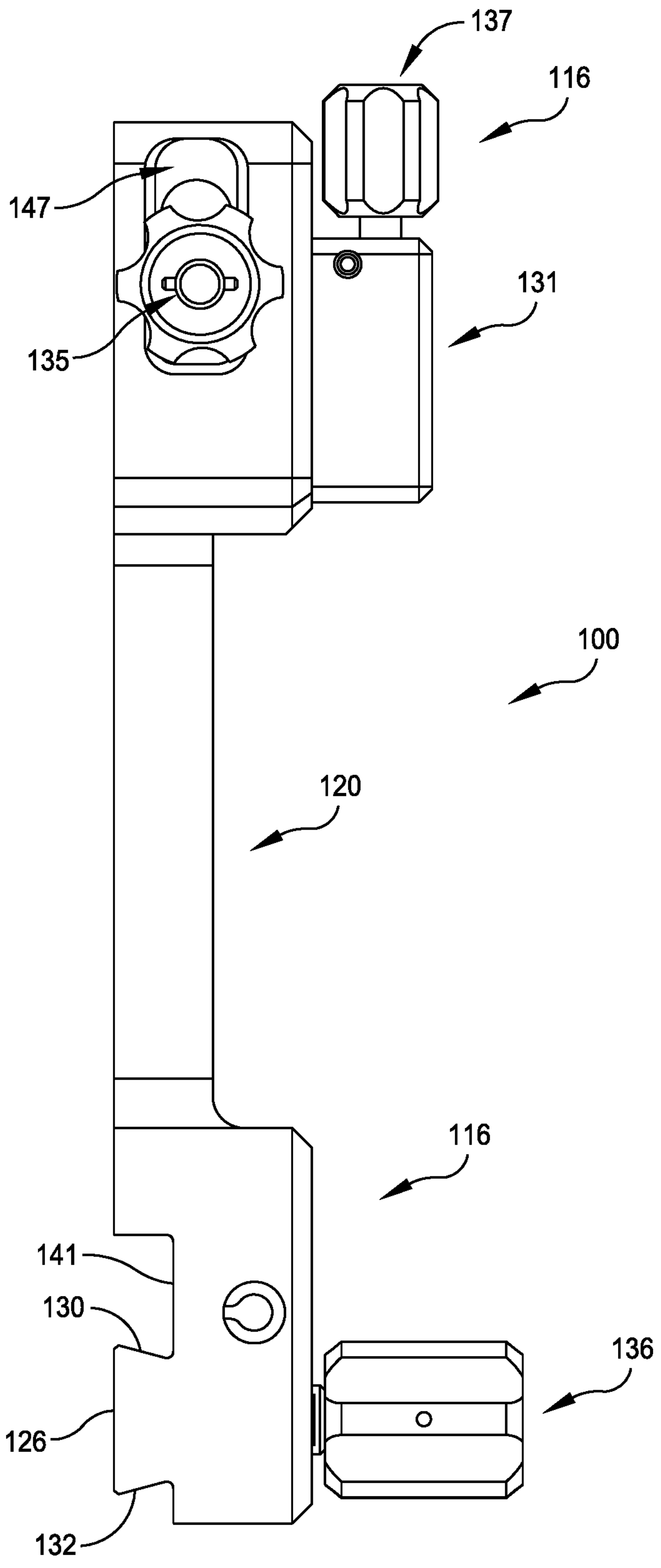
FIG. 5 is a side view of the guide illustrated in FIG. 1 that is opposite the side view of FIG. 4 in accordance with some embodiments.
Figure 6:
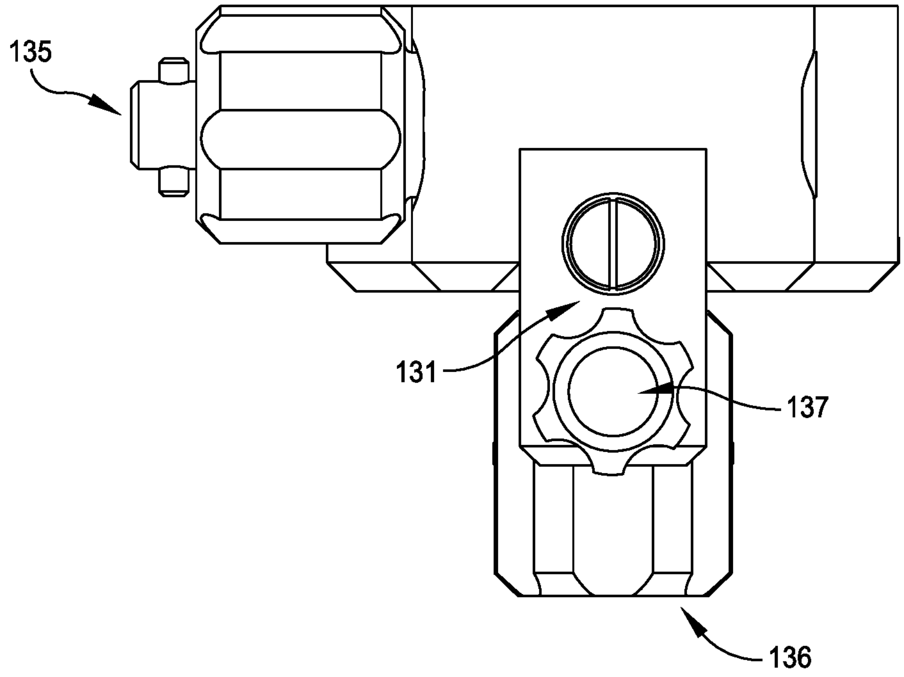
FIG. 6 is a top or superior side view of the guide illustrated in FIG. 1 in accordance with some embodiments.
Figure 7A:
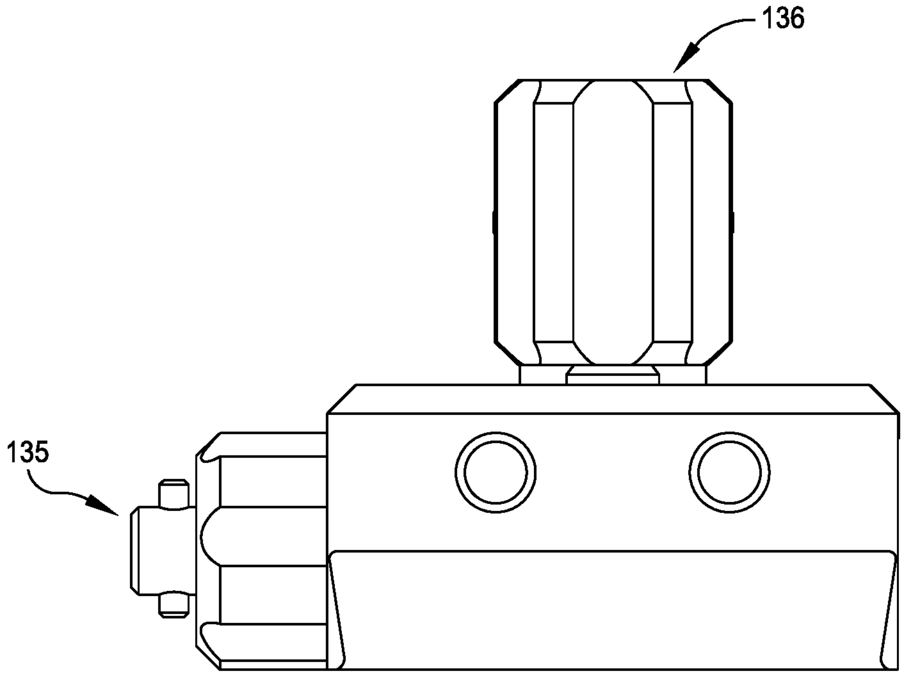
FIG. 7A is a bottom or inferior side view of the guide illustrated in FIG. 1 in accordance with some embodiments.

FIGS. 1-7 illustrate one example of a flexion/extension guide 100 in accordance with some embodiments. Guide 100 includes a body 102 extending from an inferior side 104 to a superior side 106, as seen in FIGS. 6 and 7. Body 102 further includes opposite sides 108, 110, an anterior side 112, and a posterior side 114, as seen in FIGS. 2 and 3.

In some embodiments, body 102 may be formed from a rigid radiopaque material, such as a surgical grade metal.

Body 102 comprises a wide, rectangular base 116 on the inferior side 104, a narrower, rectangular base 118 on the superior side 106, and a narrow, elongated extension 120 between bases 116 and 118. In some embodiments, body 102 is sized and configured to be installed above a joint line of a calcaneus and a talus bone, such as between a medial gutter of an ankle joint and approximately mid-way along the longitudinal axis of a tibia 260. One of ordinary skill in the art will understand that while the bases 116 and 118 are shown as having a generally rectangular shape, the bases 116 and 118 may have other shapes, e.g., square, etc.

Figure 11:
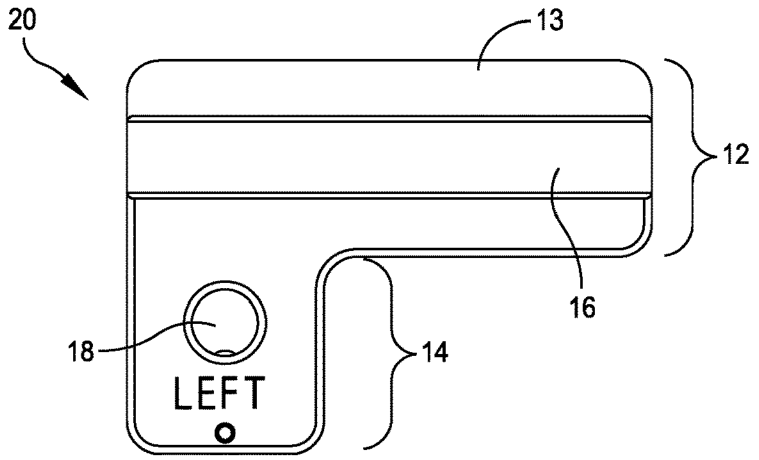
FIG. 11 is a top side view of a rotation guide slide in accordance with some embodiments.
Figure 12:
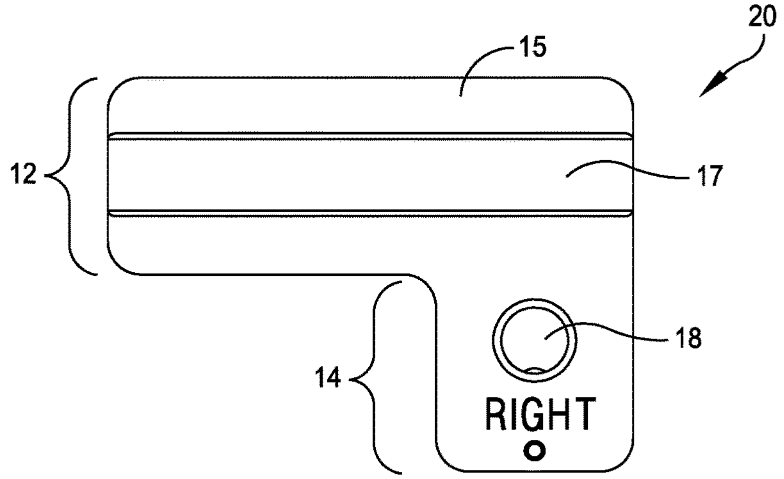
FIG. 12 is a rear end view of the rotation guide slide illustrated in FIG. 8 in accordance with some embodiments.
Figure 13:
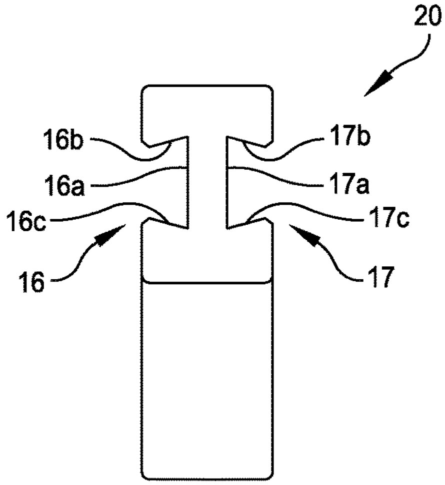
FIG. 13 is a side profile view of the rotation guide slide illustrated in FIG. 8 in accordance with some embodiments.

Base 116 includes a posterior side 122 and anterior side 124. Posterior side 122 of base 116 may include a protrusion 126 configured to engage a first channel 16 or second channel 17 of a rotation guide slide 20, as shown in FIGS. 11-13. Protrusion 126 extends longitudinally across base 116 (i.e., in a direction that is perpendicular with respect to the longitudinal length of elongated extension 120). As best seen in FIGS. 4 and 5, protrusion 126 has a flat bottom surface 128 and angled sides 130 and 132 such that the top portion of protrusion 126 is narrower than the bottom surface such that protrusion 126 has a complementary shape to channels 16 and 17 of rotation guide slide 20. In some embodiments, sides 130 and 132 of protrusion 126 perpendicularly extend from bottom surface 128 of protrusion 126. One of ordinary skill in the art will understand that while protrusion 126 is shown as having a generally flat bottom shape and continuous, protrusion 126 may have other shapes, e.g. T-slot shaped, shaped with an interruption such as a groove dividing protrusion 126 into two portions, etc.

In some embodiments, the posterior side 122 of base 116 may also include a channel 141 configured to engage side 22 or 24 of rotation guide slide 20, as described in greater detail below.

The anterior side 124 of base 116 may include an adjustment mechanism, such as knob 136 to adjust the combined rotation guide slide 20 and flexion/extension guide 100 so that extension 120 is approximately aligned with the mechanical axis of the tibia 260. Knob 136 may be connected to a screw, which locks protrusion 126 into either first channel 16 or second channel 17.

Base 116 may also include a at least one hole 138, configured to receive dowels or protrusions 210-1, 210-2 (collectively, "dowels 210" or "protrusions 210") of the angel wing alignment guide 200 as well as pins 140, 142 disposed in pin sleeves 144, 146 in accordance with some embodiments. Base 116 may also include hole 139 between at least one hole 138. Hole 139 may be used as an alignment visual cue, which provides information regarding whether the view is true and not skewed using an x-ray. One of ordinary skill in the art will understand that while at least one hole 138 is shown as having a generally round shape, at least one hole 138 may have other shapes, e.g., oblong or slot-shaped.

Base 118 includes a posterior side 123 and anterior side 125, as well as a superior side 127 and inferior side 129. In some embodiments, base 118 may include a channel 133, configured to allow movement of a rectangular engagement portion 131 disposed therein between superior side 127 and inferior side 129. Rectangular engagement portion 131 may have the ability to slide and rotate within channel 133 to enable guide 100 to set the flexion and extension angle of an ankle implant. Base 118 may also include hole or channel 147 on side 108 and a knob 135 disposed therein. Knob 135 may be configured to engage a block portion 143 on side 110 of base 118 to lock rectangular engagement portion 131 in place.

Rectangular engagement portion 131 of base 118 may include a hole 148 from the anterior side 125 to the posterior side 123, that is configured to receive pin 150 disposed in a pin sleeve 152. In some embodiments, pin sleeve 152 is rectangular and hole 148 is similarly configured to receive the rectangular shape of pin sleeve 152. Rectangular engagement portion 131 of base 118 may also include a knob 137 and extension 145 on the superior side 127 that may be rotated to allow extension 145 to be inserted into slot 154 of rectangular pin sleeve 152 to lock pin 150 in place. In some embodiments, rectangular pin sleeve 152 may have two slots 154, wherein one slot located on the superior side of the pin sleeve and one slot located on the inferior side of the pin sleeve, thereby allowing rectangular pin sleeve 152 to be inserted in either configuration and providing alignment with extension 145 in either configuration.

Figure 7B:
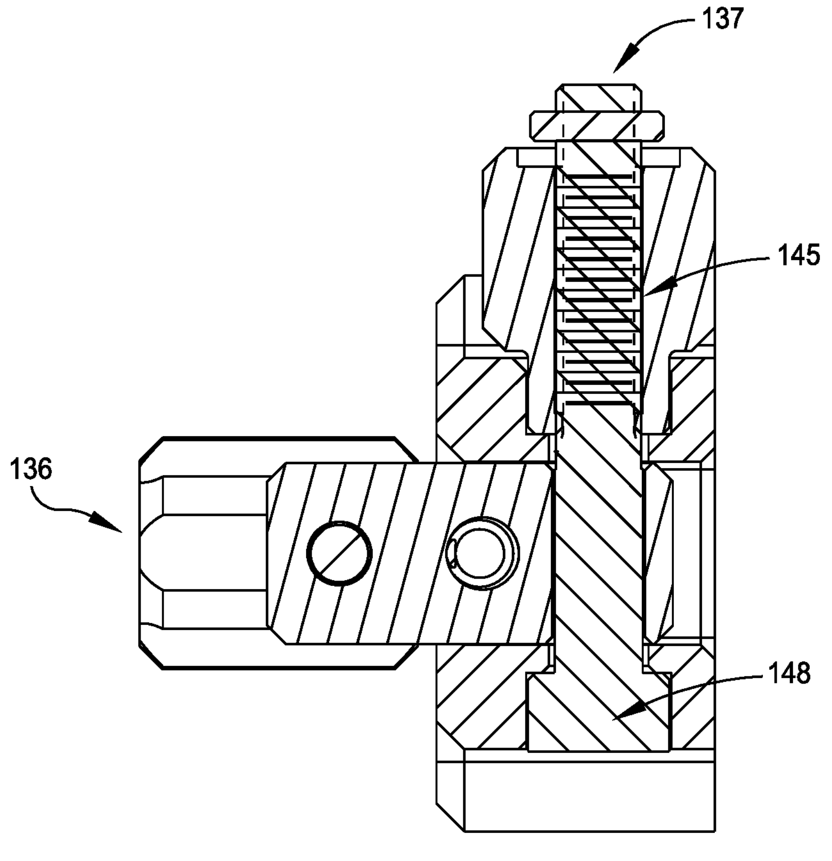
FIG. 7B is a cross-sectional view of the guide illustrated in FIG. 1, taken long its longitudinal axis, in accordance with some embodiments.

Knobs 135, 136 and 137 may be connected to screws that engage and lock their respective portions of guide 100, as shown in FIGS. 4B and 7B, which illustrate sections B-B and C-C of guide 100, taken along its longitudinal and vertical axes. Additionally, as shown in FIG. 4B, a ball and spring plunger may be used to retain rectangular pin sleeve 152.

Figure 8:
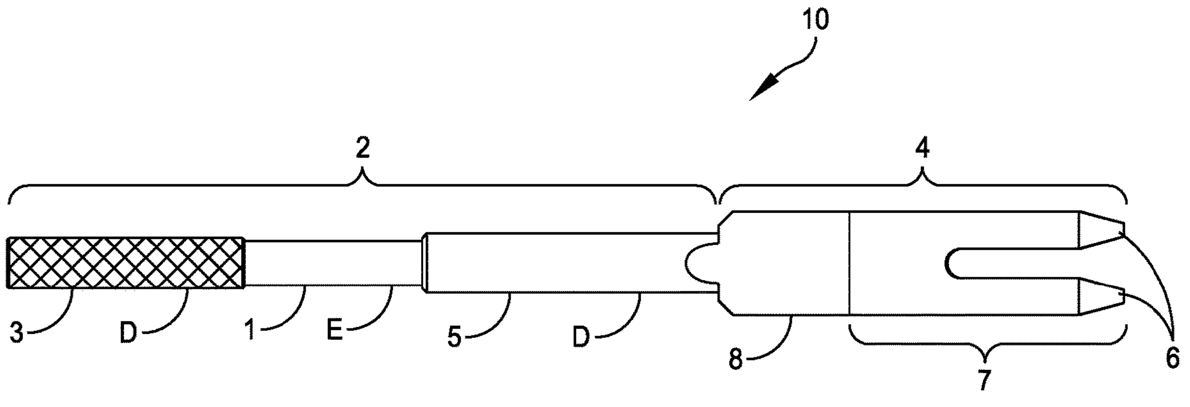
FIG. 8 is a top side view of one example of a medial gutter fork in accordance with some embodiments.
Figure 9:
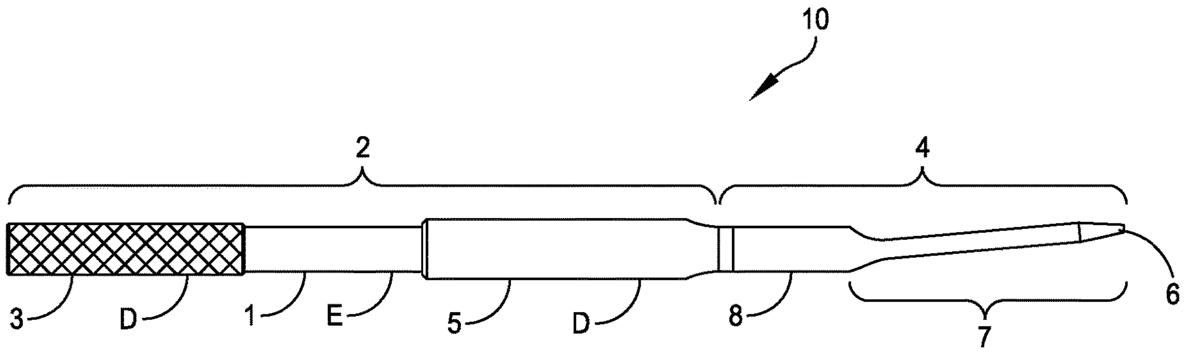
FIG. 9 is a rear end view of the medial gutter fork illustrated in FIG. 8 in accordance with some embodiments.
Figure 10:
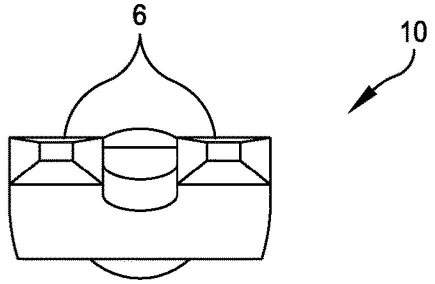
FIG. 10 is a front end view of the medial gutter fork illustrated in FIG. 8 in accordance with some embodiments.

Referring to FIGS. 8-10, a medial gutter fork 10 includes a shaft 2 and a head 4. In some embodiments, shaft 2 has a cylindrical geometry and includes a proximal end 3 and a distal end 5 each being of a first diameter D, and an inner section 1 disposed between proximal end 3 and distal end 5 and having a second diameter E. In some embodiments, the first diameter D is greater than second diameter E. Head 4 has a transitional portion 8, which is connected to the distal end 5 of shaft 2, and a forked portion 7 including a pair of prongs 6. Medial gutter fork 10 is configured to be inserted into the medial gutter of an ankle joint to serve as a reference point to additional elements of guides for determining the proper placement and angle of an ankle implant. In some embodiments, the head 4 does not have a forked shape. One of ordinary skill in the art will understand that the angle of an ankle implant may include 0 degrees.

Referring to FIGS. 11-13, rotation guide slide 20 has an "L" shaped body including a first portion 12 extending longitudinally in a first direction and a second portion 14 extending laterally from the first portion 12 in a second direction. In some embodiments, first portion 12 is longer than second portion 14 and the first and second directions are perpendicular with respect to one another. One of ordinary skill in the art will understand that while first portion 12 is shown as longer than second portion 14, first portion 12 may be a different length, e.g., equal to or shorter than second portion 14. First portion 12 defines a first channel 16 that runs the length of first portion 12 on a first side 13 and defines a second channel 17 on second side 15, which is disposed opposite the first side 13. Second portion 14 defines a guide hole 18 which is configured to engage the shaft 2 of medial gutter fork 10. In some embodiments, hole 18 is located at the approximate center of second portion 14; however, hole 18 can be located at other positions of second portion 14.

FIG. 13 illustrates one example of a configuration of channel 16 in accordance with some embodiments. Channel 16 is illustrated as having a flat bottom surface 16 *a* and angled side walls 16 *b* and 16 *c* that taper inwardly such that the top of channel 16 is narrower than the bottom. Second channel 17 is aligned along the same longitudinal axis as first channel 16 and is shaped identical to first channel 16 with a flat bottom surface 17 *a* and angled side walls 17 *b* and 17 *c* that taper inwardly such that the top of channel 17 is narrower than the bottom. One of ordinary skill in the art will understand that while channels 16 and 17 are shown as having generally flat bottom shapes, channels 16 and 17 may have other shapes, e.g. T-slot shaped, etc.

Either first channel 16 or second channel 17 faces away from the ankle and will engage with flexion/extension guide 100 as described in greater detail below. This configuration enables rotation guide slide 20 to be used during an ankle replacement procedure for either the left ankle or right ankle.

The guide 100 with medial gutter fork 10 and rotation guide slide 20 is now briefly described with reference to FIGS. 14-15, which is used once access is gained to the tibia 260 and talus 265.

Figure 14:
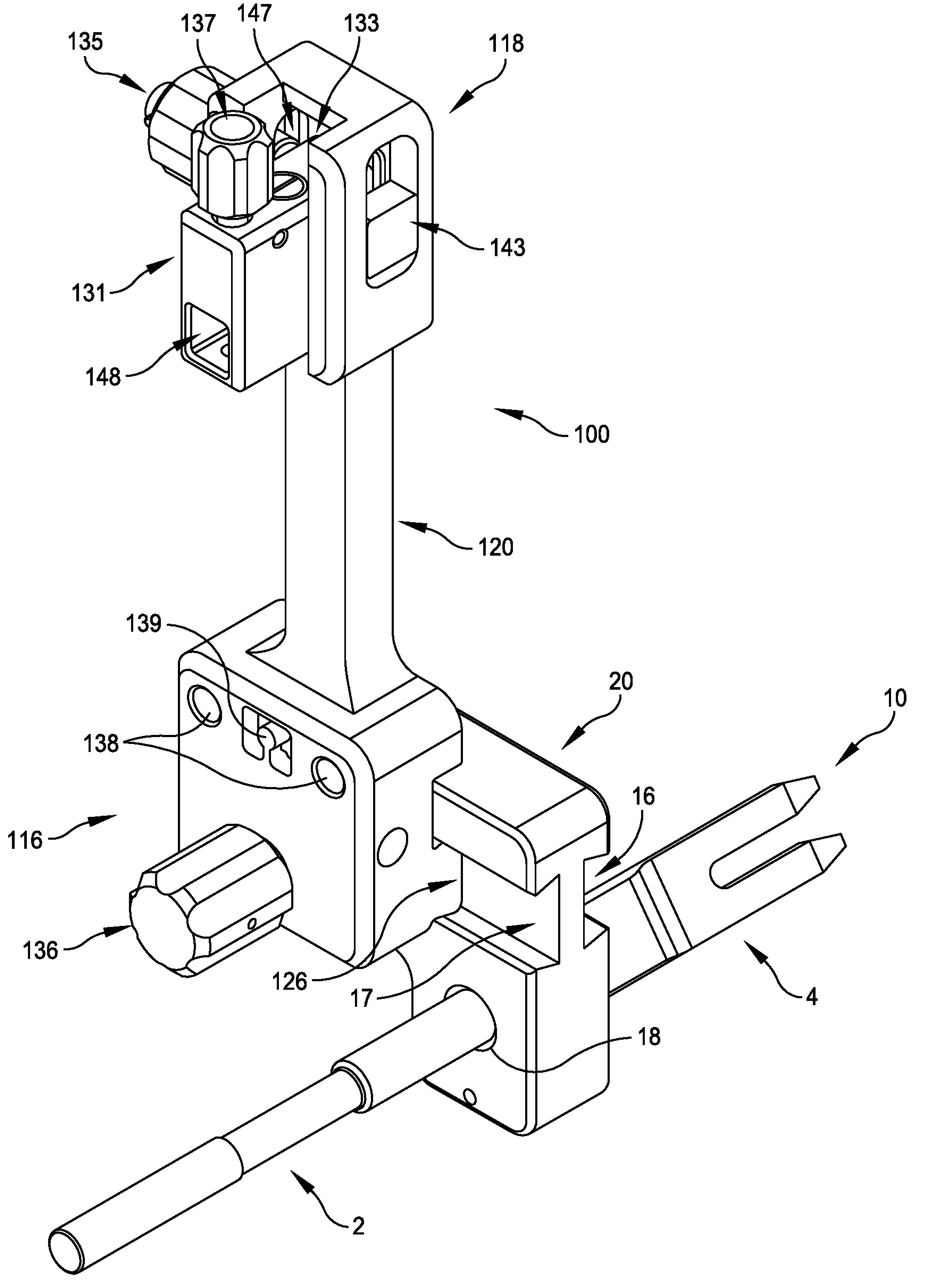
FIG. 14 is an isometric view of the rotation guide slide illustrated in FIG. 11 coupled to the guide illustrated in FIG. 1 and the medial gutter fork illustrated in FIG. 8, in accordance with some embodiments.
Figure 15:
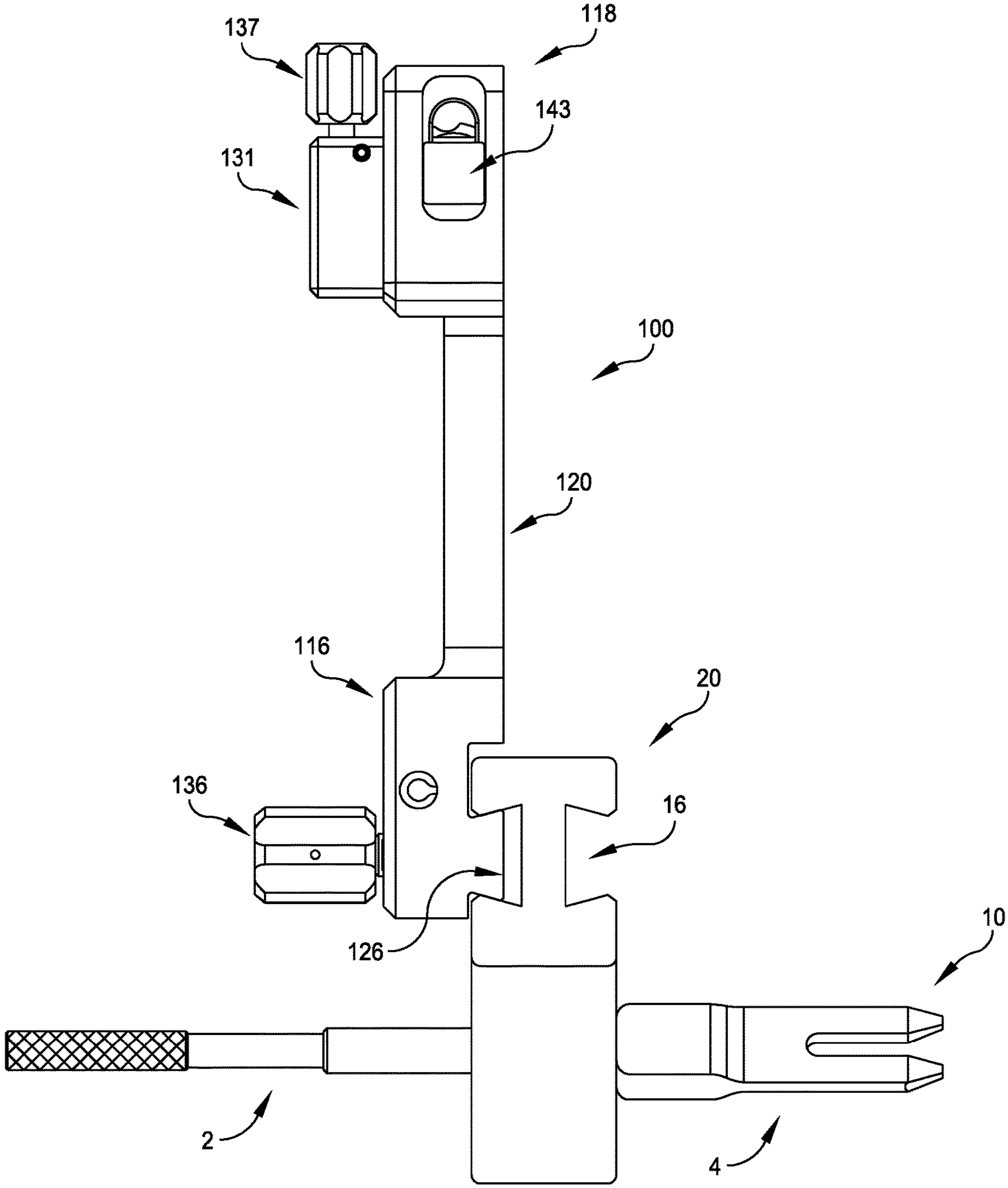
FIG. 15 is a side view of the rotation guide slide illustrated in FIG. 11 coupled to the guide illustrated in FIG. 1 and the medial gutter fork illustrated in FIG. 8, in accordance with some embodiments.

Gutter fork 10 is inserted into the medial gutter of the ankle joint, and rotation guide slide 20 is operationally connected to medial gutter fork 10 by placing guide hole 18 over distal end 5 of shaft 2 as illustrated in FIG. 14. Rotation guide slide 20 is positioned with either first channel 16 or second channel 17 facing away from the tibia 260. Flexion/extension guide 100 is operationally connected to rotation guide slide 20 by sliding protrusion 126 into either first channel 16 or second channel 17, whichever is facing away from the tibia 260. Thus assembled, an operator uses knob 136 to lock the mediolateral translation location of rotation guide slide 20 and flexion/extension guide 100 about an axis defined by the shaft of the tibia 260.

Figure 16:
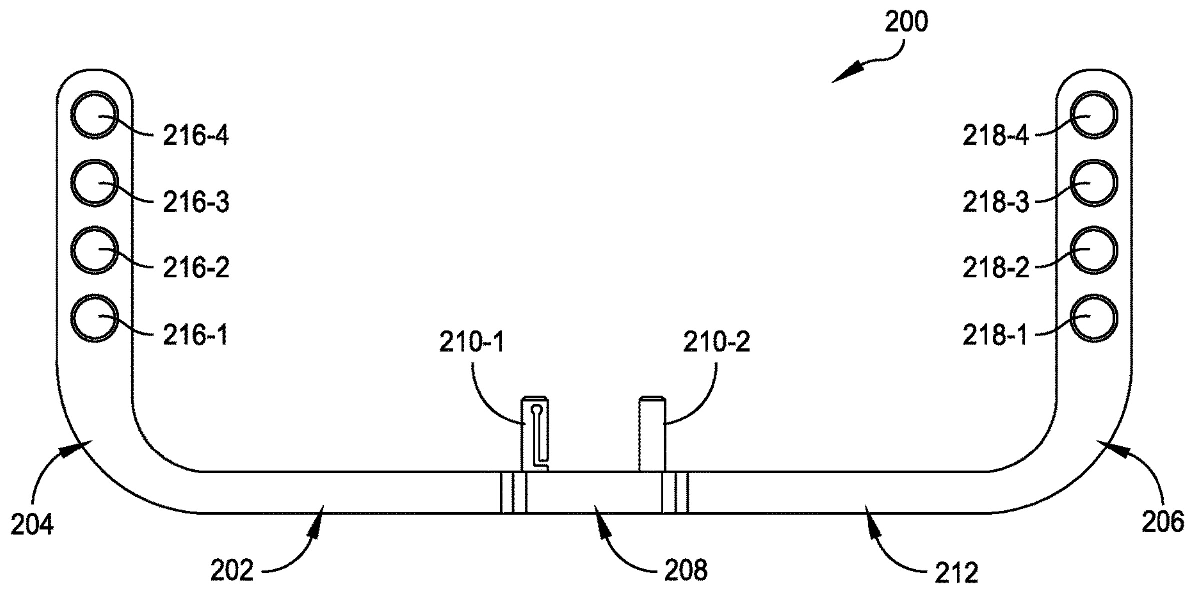
FIG. 16 is a top side view of one example of an alignment guide in accordance with some embodiments.
Figure 17:
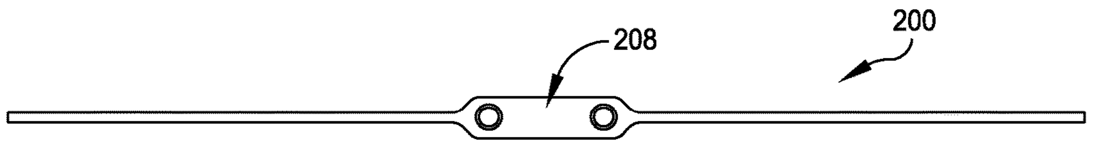
FIG. 17 is a rear end view of the alignment guide illustrated in FIG. 16 in accordance with some embodiments.
Figure 18:
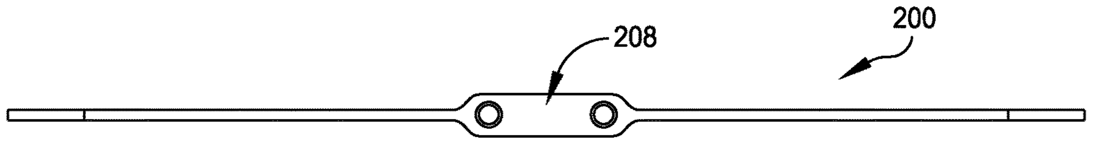
FIG. 18 is a front end view of the alignment guide illustrated in FIG. 16 in accordance with some embodiments.
Figure 19:
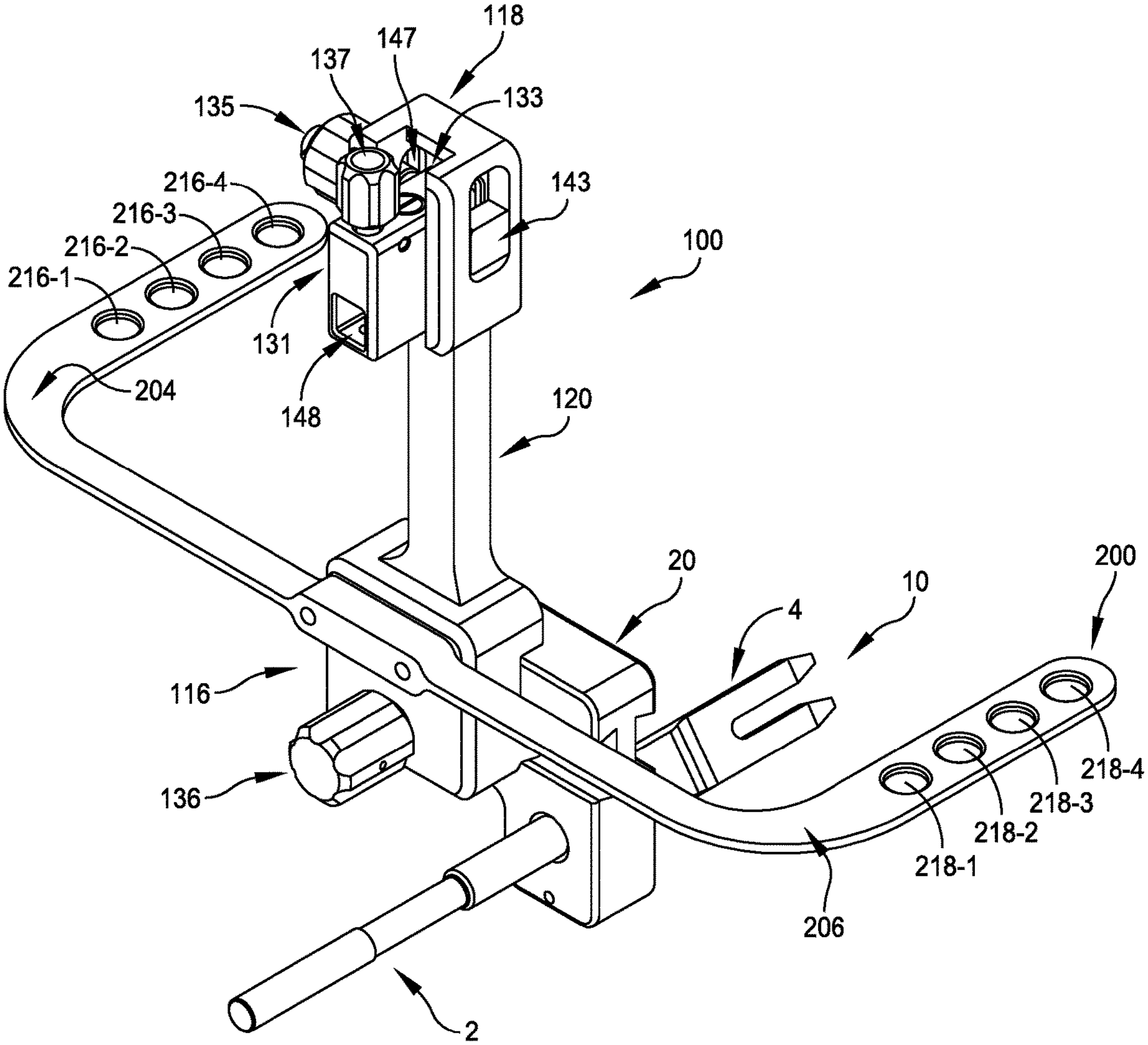
FIG. 19 is an isometric view of the alignment guide illustrated in FIG. 16 coupled to the guide illustrated in FIG. 1, in accordance with some embodiments.
Figure 20:
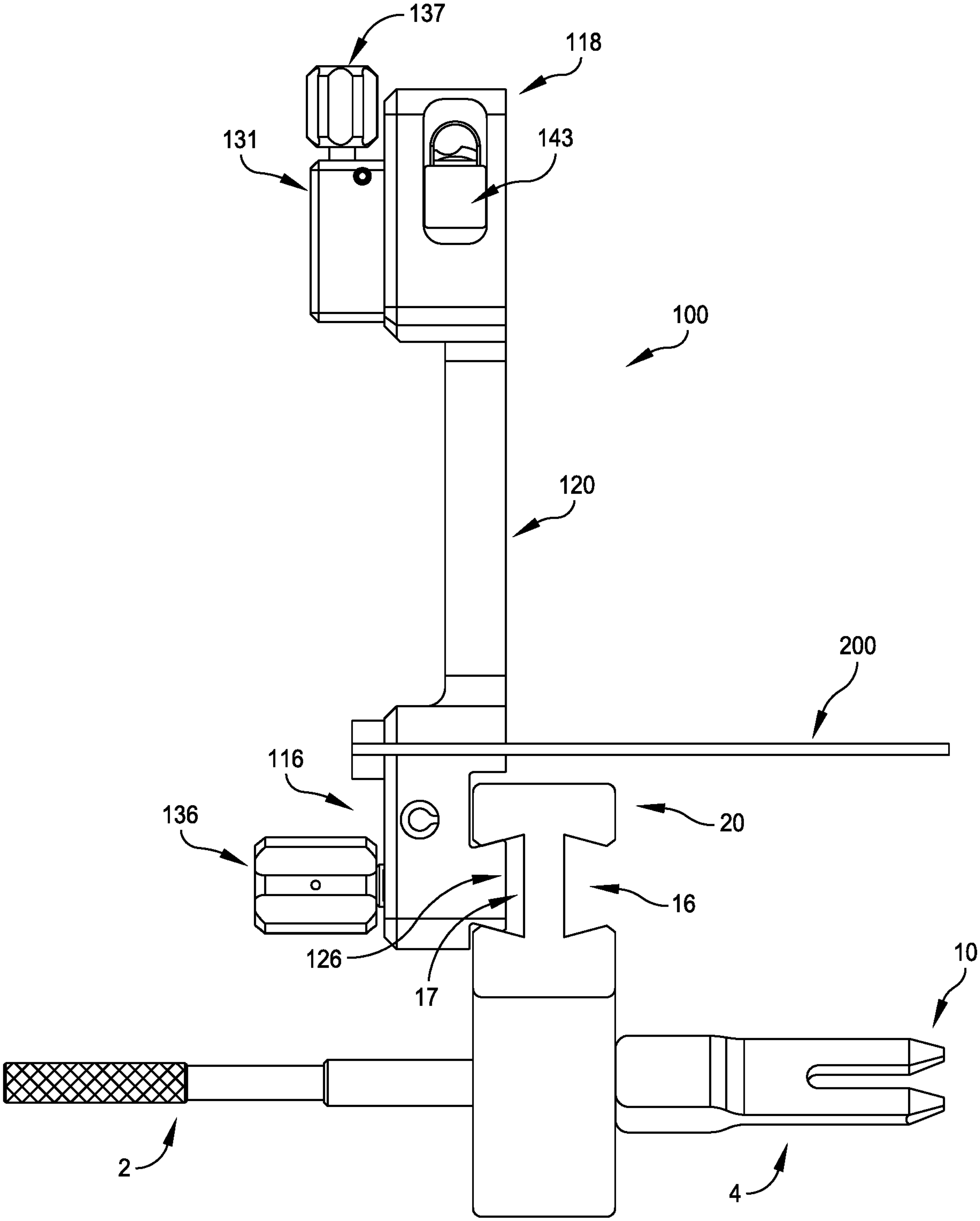
FIG. 20 is a side view of the alignment guide illustrated in FIG. 16 coupled to the guide illustrated in FIG. 1, in accordance with some embodiments.

Referring to FIGS. 16-18, angel wing alignment guide 200 may have a generally arcuate or "u-shaped" body with a transverse beam 202 extending between a first arm 204 and a second arm 206. As best seen in FIGS. 17 and 18, the transverse beam 202 may include an enlarged area 208, which may have a width that is greater than a width of a remainder of the transverse beam 202 and/or a width of arms 204, 206. In some embodiments, one or more dowels or protrusions 210-1, 210-2 (collectively, "dowels 210" or "protrusions 210") extend from a posterior surface 212 of alignment guide 200. Protrusions 210 are sized and configured to be received within at least one hole 138 defined by base 116 of guide 100 for coupling the alignment guide 200 to guide 100 as best seen in FIGS. 19-20. One of ordinary skill in the art will understand that while the protrusions 210 are shown as having a generally circular cross-sectional shape, which a cross section is taken along an axis perpendicular to a longitudinal axis of the protrusions, the protrusions 210 may have other cross-sectional shapes, e.g., triangular, rectangular, etc.

In some embodiments, arms 204 includes one or more holes 216-1, 216-2, 216-3, 216-4 (collectively, "holes 216"), and arm 206 includes one or more holes 218-1, 218-2, 218-3, 218-4 (collectively, "holes 218"). Holes 216, 218 are sized and configured to receive a dowel, pin, rod, or other elongate radiopaque device, such as alignment rod 270 illustrated in FIGS. 21-23. The alignment rod 270 may be coupled to the alignment guide 200 to provide a surgeon with a mediolateral view to approximate an axis of a tibial implant that is to be implanted. The alignment guide 200 can also provide a surgeon with an anteroposterior view to approximate the mechanical axis of a tibial implant. Using alignment guide 200 and alignment rod 270, the surgeon can assess the proper location of a cutting and/or reaming guide with a mechanical and/or anatomic axis of the patient. Although a plurality of holes is shown in FIG. 16 to provide the surgeon with multiple locations at which the alignment rod 270 may be positioned, it should be understood that a single hole may be provided, or one or more slots may be provided along the longitudinal axes of the arms 204, 206 to provide the surgeon with the ability to provide near continuous adjustment of the location of such an alignment rod 270.

Figure 21:
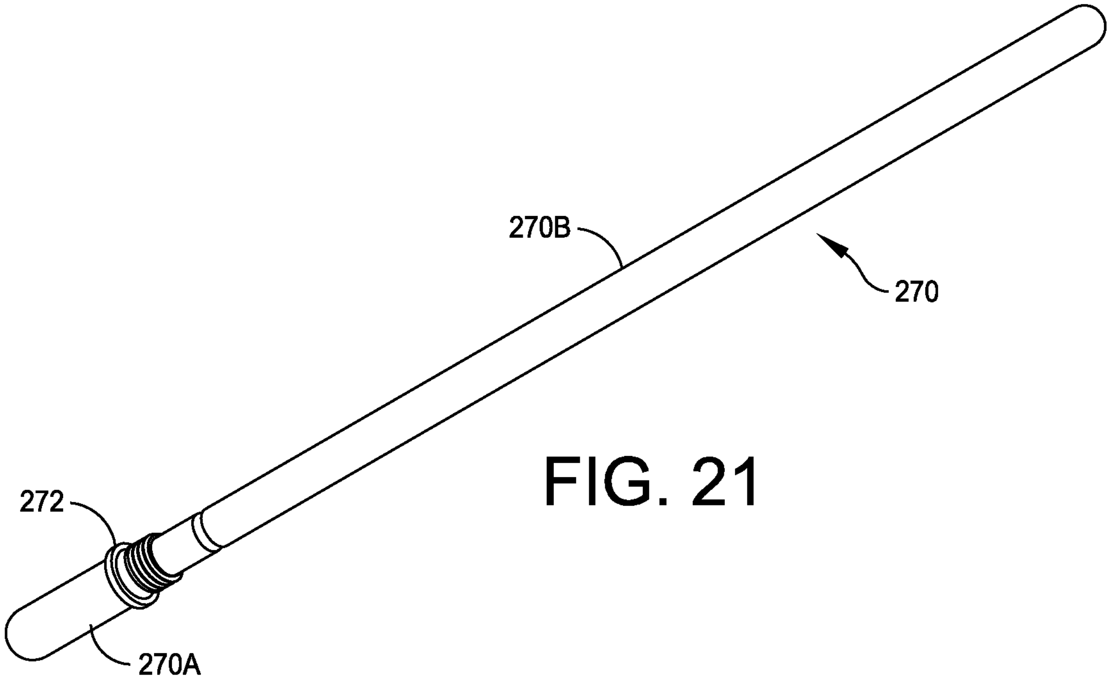
FIG. 21 is a top side view of another example of an alignment guide in accordance with some embodiments.
Figure 22:
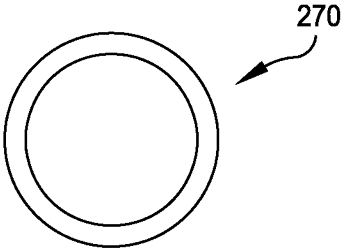
FIG. 22 is a distal end view of the alignment guide illustrated in FIG. 21 in accordance with some embodiments.
Figure 23:
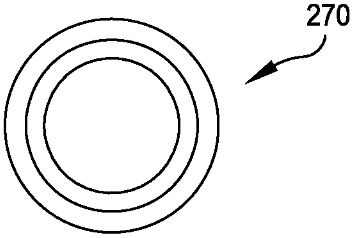
FIG. 23 is a proximal end view of the alignment guide illustrated in FIG. 21 in accordance with some embodiments.
Figure 24:
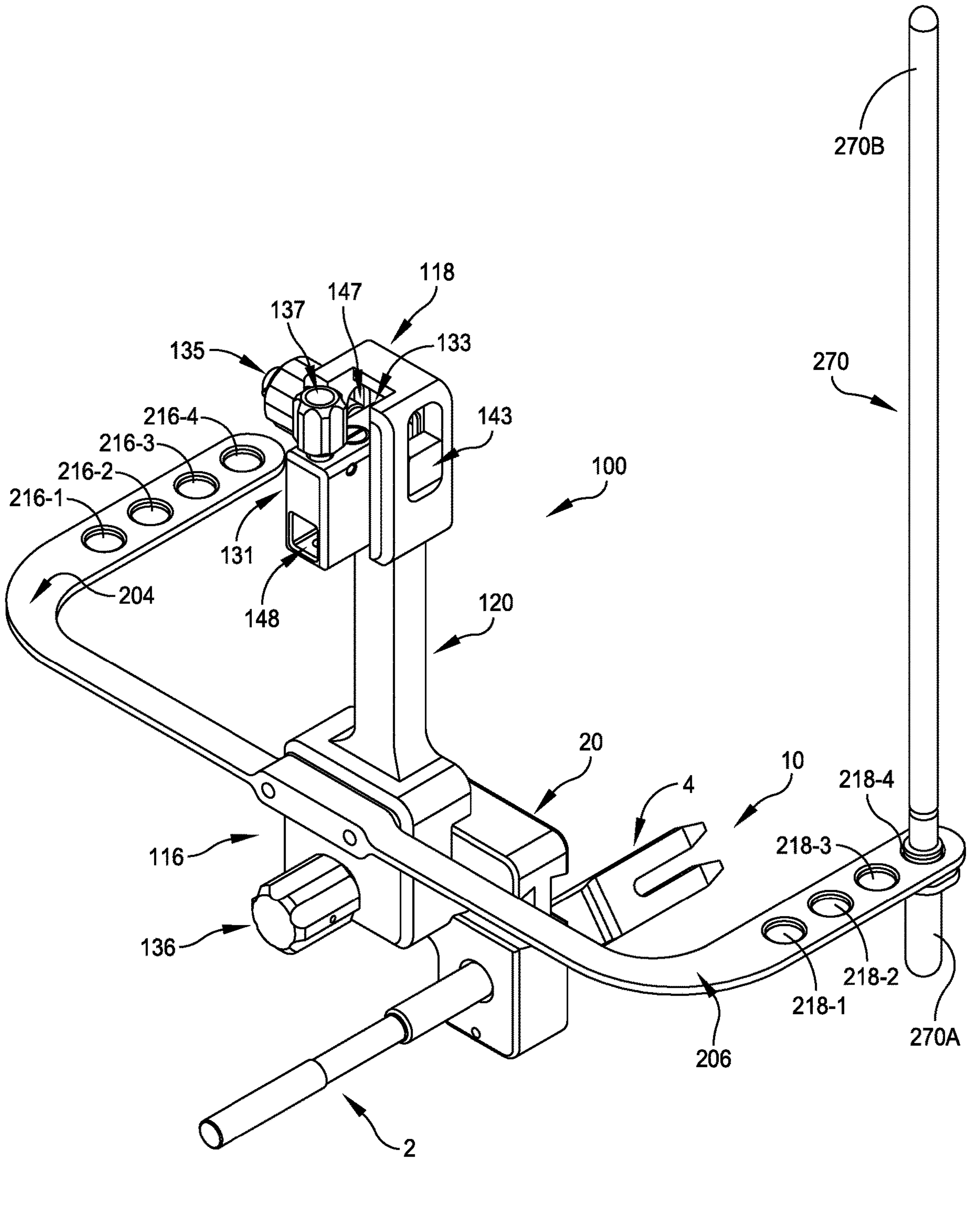
FIG. 24 is an isometric view of the alignment guide illustrated in FIG. 21 coupled to the alignment guide illustrated in FIG. 16, which is coupled to the guide illustrated in FIG. 1, which is coupled to the rotation guide slide illustrated in FIG. 11, which is coupled to the medial gutter fork illustrated in FIG. 8, in accordance with some embodiments.
Figure 25:
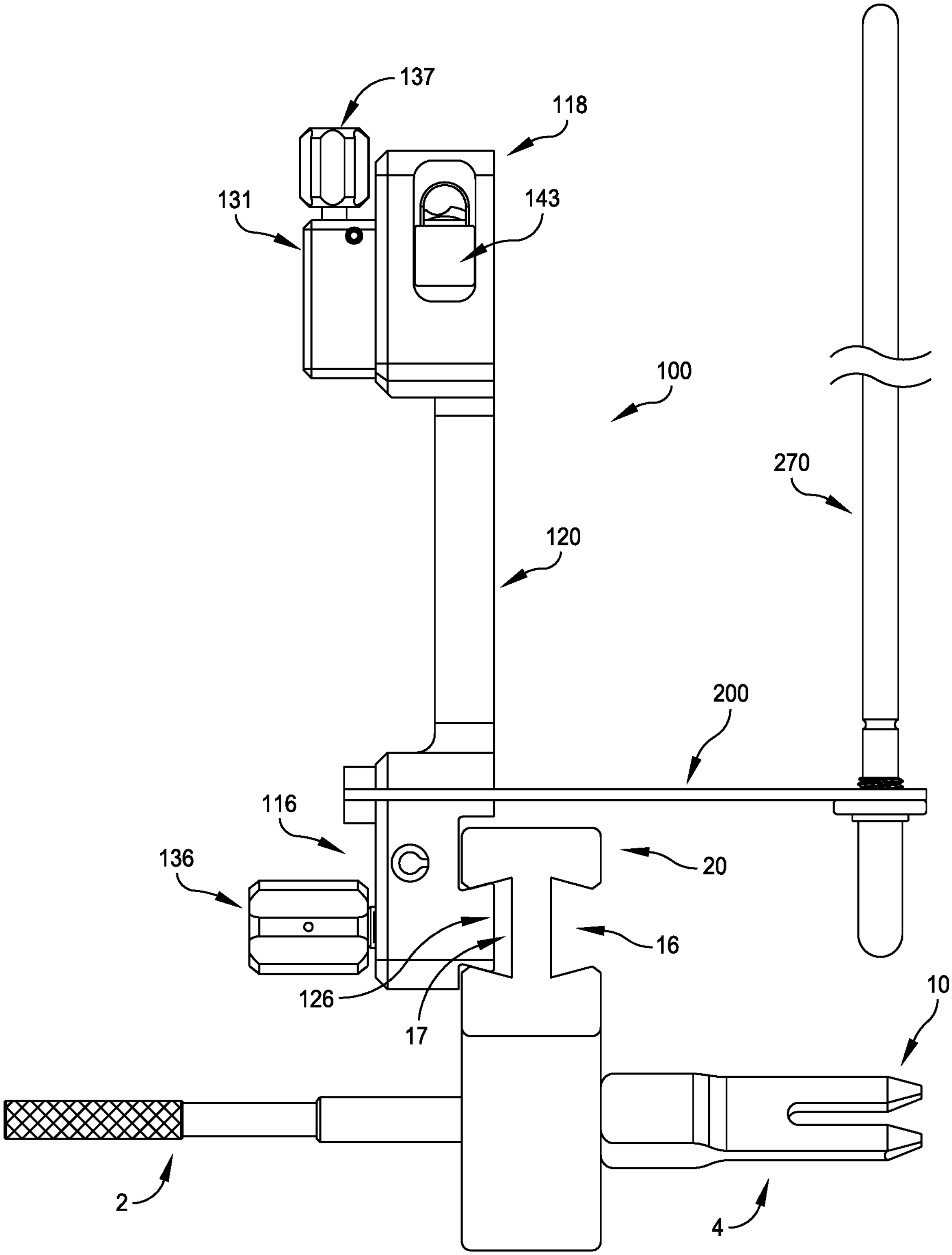
FIG. 25 is a side view of the alignment guide illustrated in FIG. 21 coupled to the alignment guide illustrated in FIG. 16, which is coupled to the guide illustrated in FIG. 1, which is coupled to the rotation guide slide illustrated in FIG. 11, which is coupled to the medial gutter fork illustrated in FIG. 8, in accordance with some embodiments.
Figure 26:
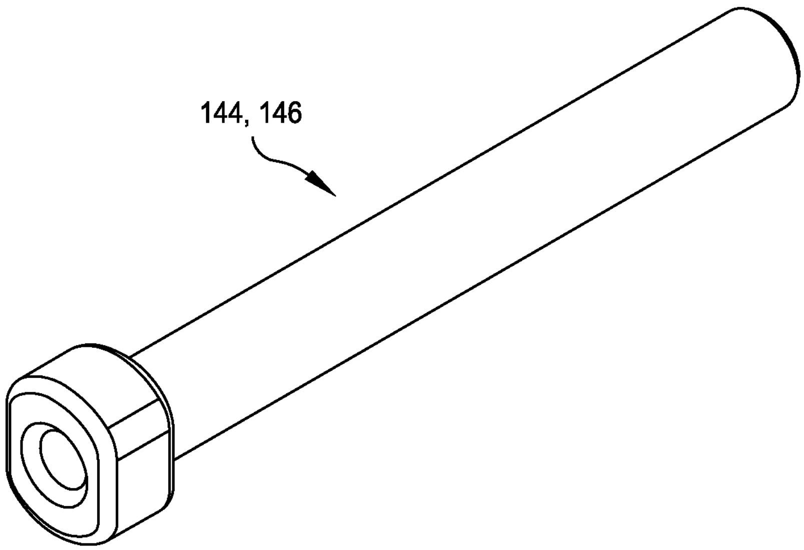
FIG. 26 is an isometric view of one example of a pin sleeve that may be used with the guide illustrated in FIG. 1 in accordance with some embodiments.
Figure 27:
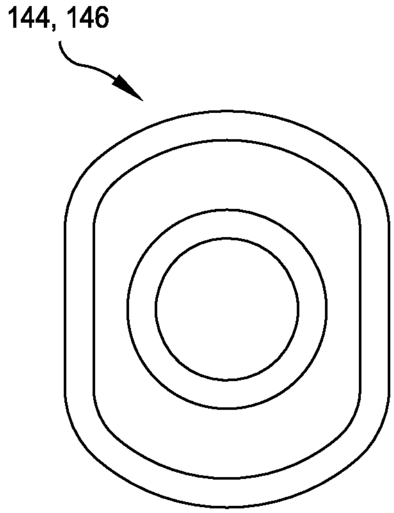
FIG. 27 is a front end view of the pin sleeve illustrated in FIG. 26 in accordance with some embodiments.
Figure 28:
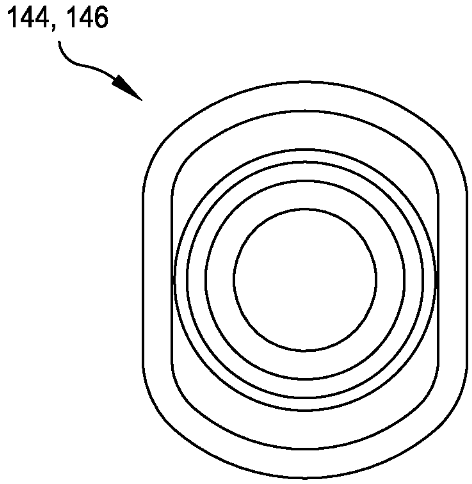
FIG. 28 is a rear end view of the pin sleeve illustrated in FIG. 26 in accordance with some embodiments.
Figure 29:
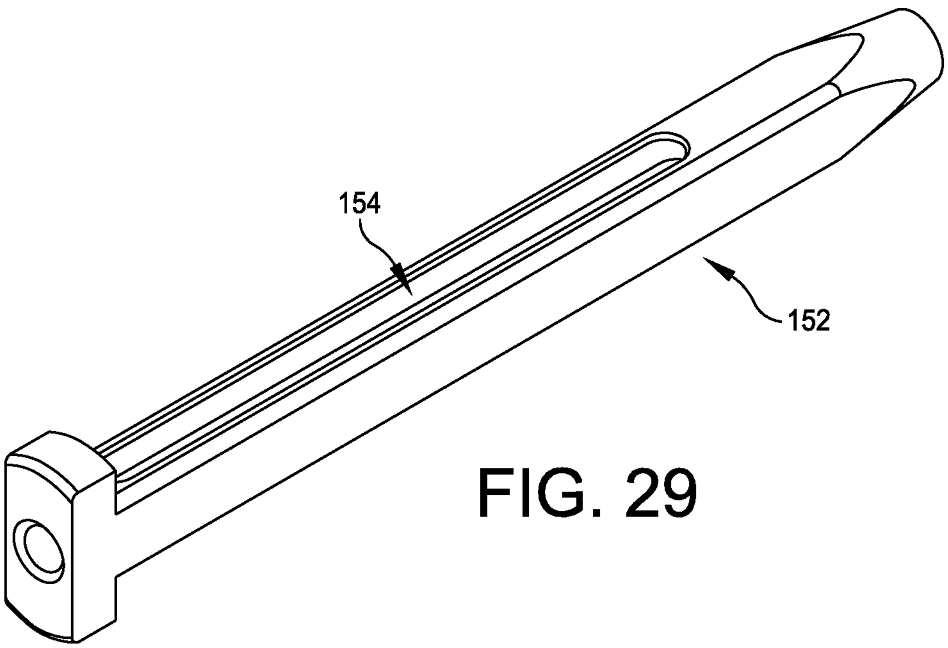
FIG. 29 is an isometric view of another example of a pin sleeve that may be used with the guide illustrated in FIG. 1 in accordance with some embodiments.
Figure 30:
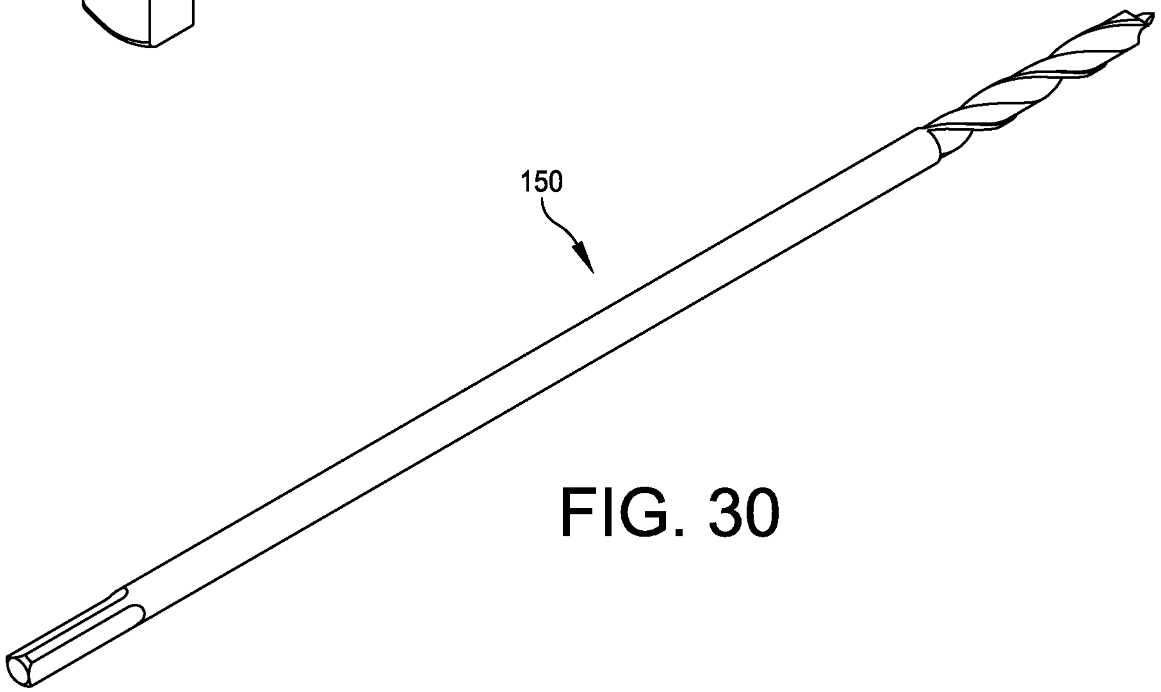
FIG. 30 is an isometric view of one example of a pin that may be used with the guide illustrated in FIG. 1 in accordance with some embodiments.

In some embodiments, alignment rod 270 has an elongate body that includes a stop collar 272 disposed along its length to divide alignment rod 170 into unequal portions 270A and 270B. As shown in FIGS. 21-23, portion 270A is shorter than portion 270B.

The installation of angel wing alignment guide 200 and alignment rod 270 are described briefly with reference to FIGS. 19-20 and 24-25.

In some embodiments, the angel wing alignment guide 200 is attached to the flexion/extension guide 100 by inserting the angel wing alignment guide protrusions 210 into the at least one hole 138 of base 116. In some embodiments, the position of the angel wing alignment guide 200 is viewed under A/P fluoroscopy to establish coronal alignment, which is typically parallel to the natural joint line.

Portion 270B of alignment rod 270 is inserted through one of the holes 216, 218 of the angel wing alignment guide 200, until stop collar 272 abuts angle wing alignment guide 200. The position of the alignment rod 270 can be viewed under lateral fluoroscopy to establish sagittal rotation, which is typically parallel to a shaft of the tibia 260. Knob 135 may be turned to lock rectangular engagement portion 131 of base 118 in place after the desired alignment is achieved.

Figure 31:
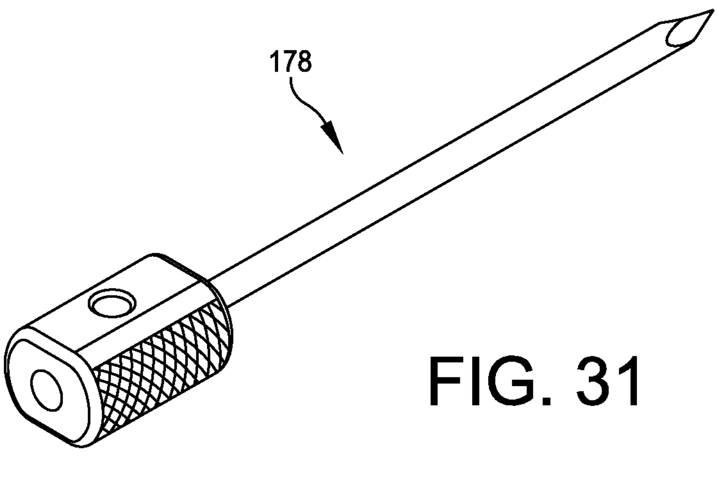
FIG. 31 is an isometric view of one example of a trocar that may be used with the guide illustrated in FIG. 1 in accordance with some embodiments.
Figure 32:
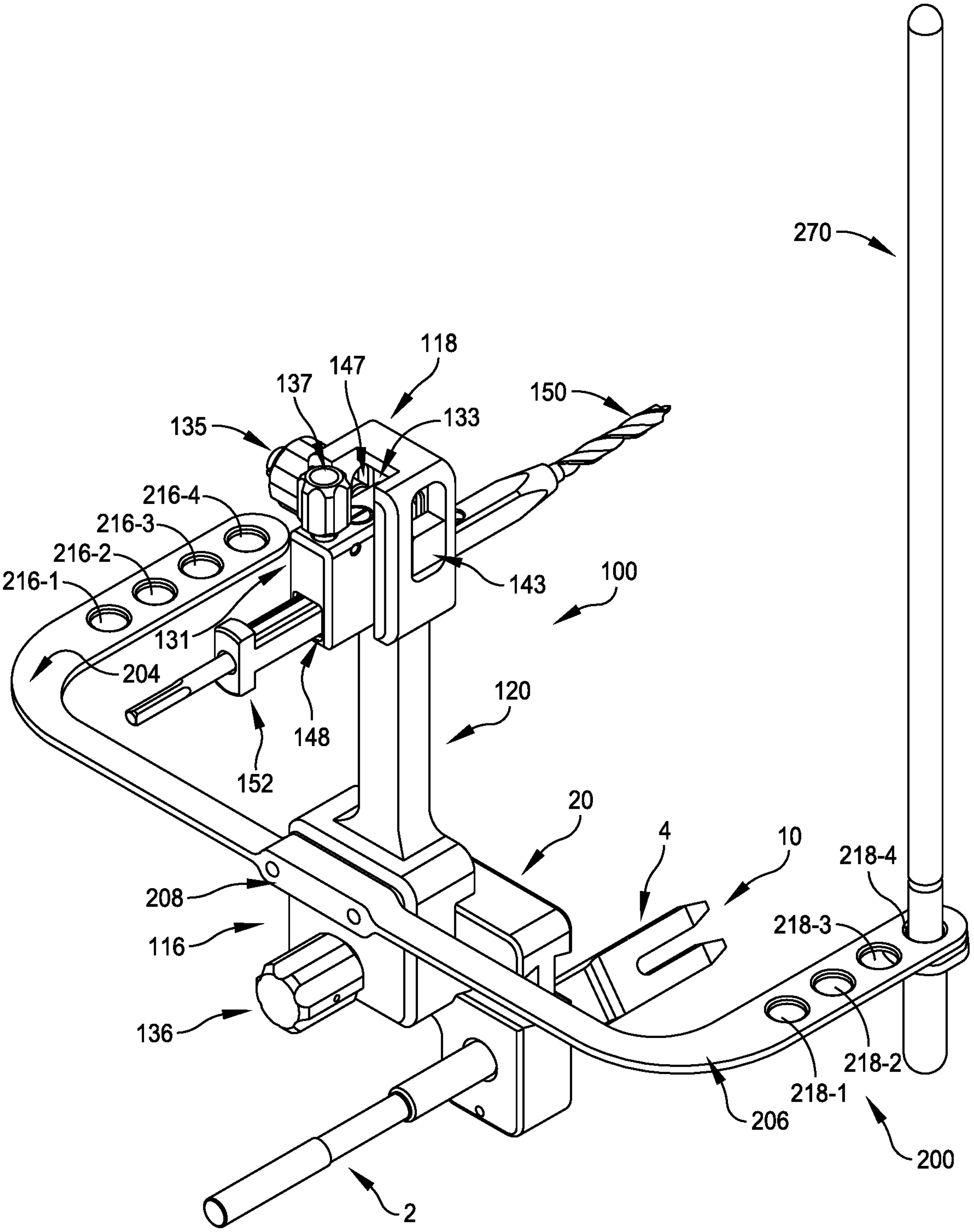
FIG. 32 is an isometric view of the pin sleeve illustrated in FIG. 29 and a pin illustrated in FIG. 30 disposed within a hole defined by the proximal end of the guide illustrated in FIG. 1, which is coupled to the alignment guides as illustrated in FIGS. 16 and 21, in accordance with some embodiments.
Figure 33:
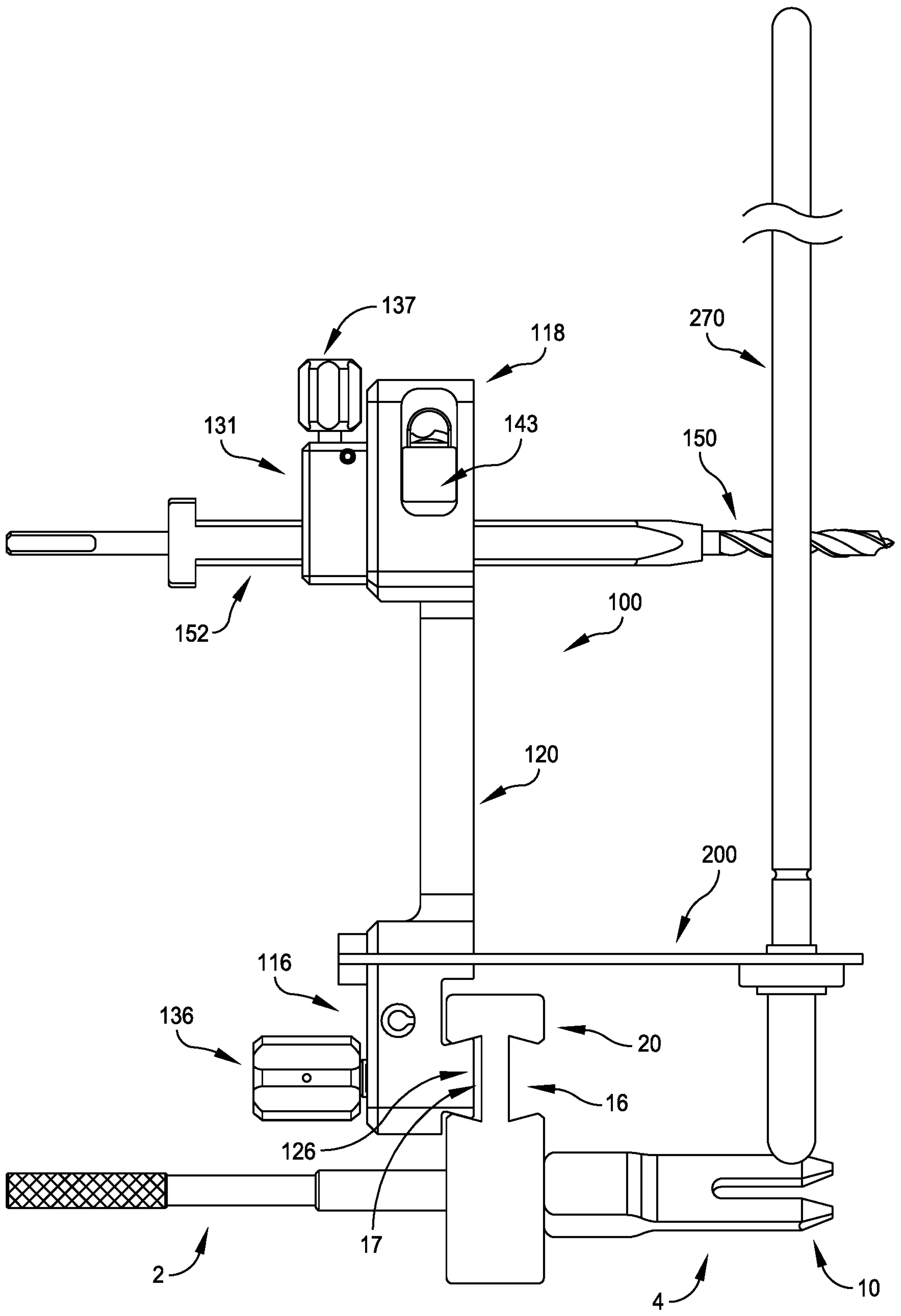
FIG. 33 is a side view of the pin sleeve illustrated in FIG. 29 and a pin illustrated in FIG. 30 disposed within the hole defined by the proximal end of the guide illustrated in FIG. 1, which is coupled to the alignment guides as illustrated in FIGS. 16 and 21, in accordance with some embodiments.

As illustrated in FIGS. 29-30 and 32-33, pin sleeve 152 is inserted into hole 148 of rectangular engagement portion 131 of base 118 of the flexion/extension guide 100. A trocar, such as trocar 178 illustrated in FIG. 31, may be inserted into the pin sleeve 152 to create a "stab wound" or indentation in the bone to prevent skiving for drilling of a percutaneous pin. The trocar 178 is then removed. A guide pin 150 is inserted into pin sleeve 152 and through the tibia 260. Knob 137 may then be turned to allow extension 145 to be inserted into slot 154 of pin sleeve 152 to lock pin 150 in place.

While the flexion/extension guide 100, rotation guide slide 20, angel wing alignment guide 200, alignment rod 270 and pin sleeve 152 are described as being operationally connected to medial gutter fork 10 after it is inserted into the medial gutter of the ankle joint, one of ordinary skill in the art will understand that the flexion/extension guide 100, rotation guide slide 20, angel wing alignment guide 200, alignment rod 270 and pin sleeve 152 may be assembled prior to placing guide hole 18 of rotation guide slide 20 over the distal end 5 of shaft 2 of the medial gutter fork 10. Thus a surgeon may place the entire assembly of flexion/extension guide 100, rotation guide slide 20, angel wing alignment guide 200, alignment rod 270 and pin sleeve 152 over the distal end 5 of shaft 2 of the medial gutter fork 10 through guide hole 18 of rotation guide slide 20. A surgeon may then adjust the alignment of the guides and use knob 136 to lock the mediolateral translation location of rotation guide slide 20 and flexion/extension guide 100. A trocar 178 may then be inserted into the pin sleeve 152 and removed. Guide pin 150 may then be inserted into pin sleeve 152 and through the tibia 260. Knob 135 may then be used to lock rectangular engagement portion 131 in place and knob 137 may be used to allow extension 145 to be inserted into slot 154 of pin sleeve 152 to lock pin 150 in place.

Figure 34:
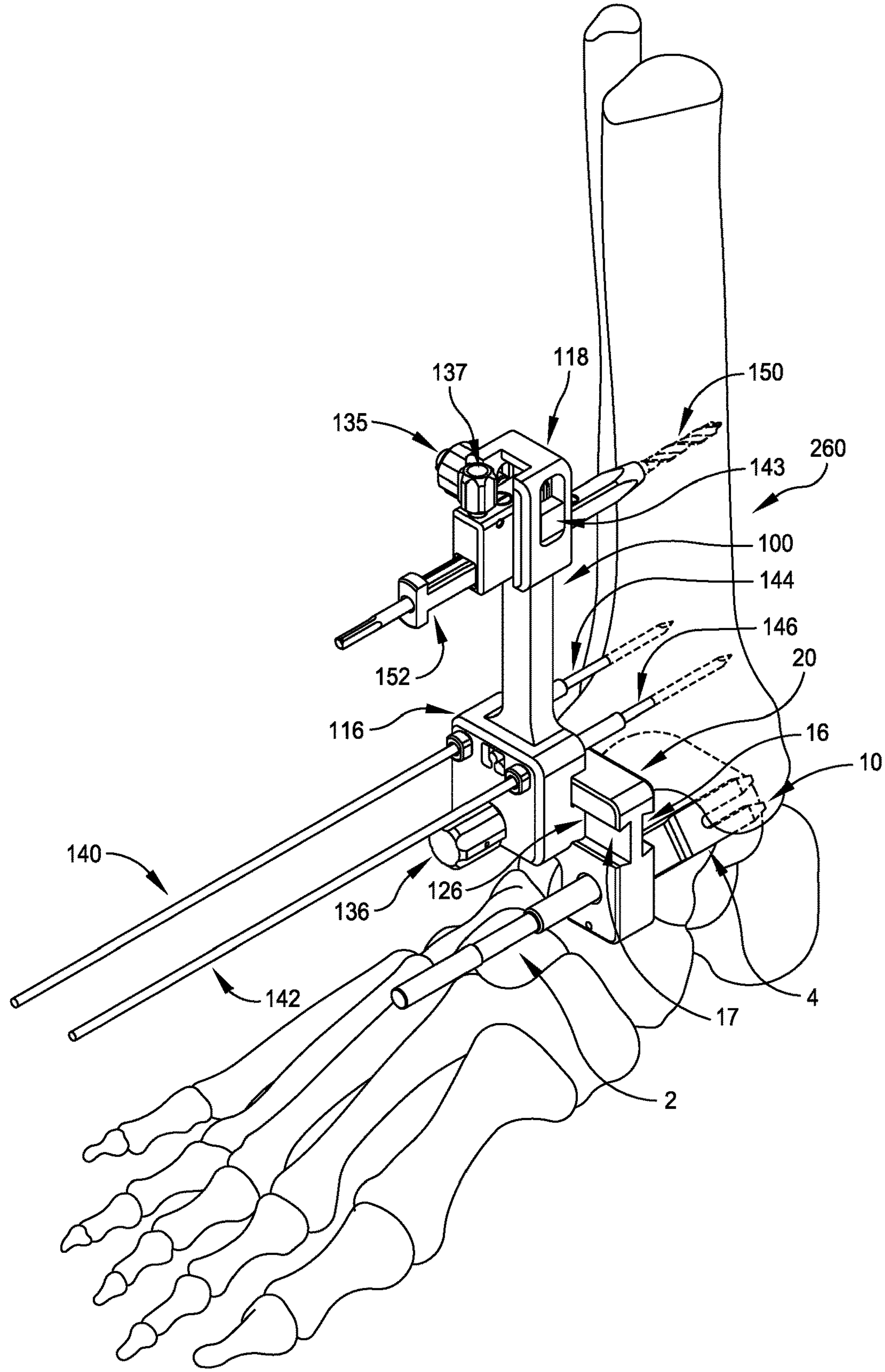
FIG. 34 is an isometric view of a plurality of pins disposed within pin sleeves illustrated in FIG. 26, which are disposed within a plurality of holes defined by the distal end of the guide illustrated in FIG. 1, and a pin illustrated in FIG. 30 disposed within the pin sleeve illustrated in FIG. 29, which is disposed within the hole defined by the proximal end of the guide illustrated in FIG. 1, in accordance with some embodiments.
Figure 35:
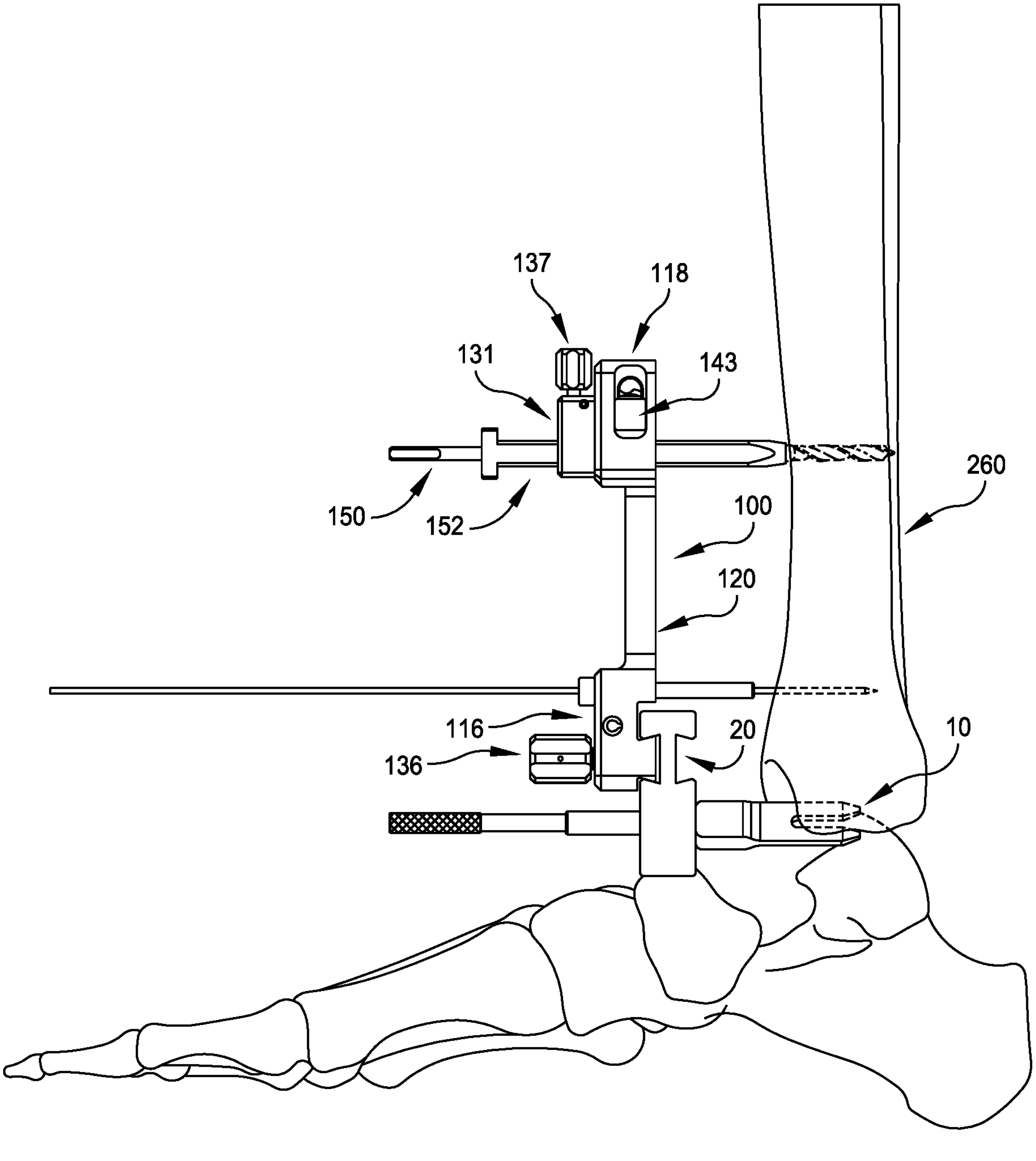
FIG. 35 is a side view of a plurality of pins disposed within pin sleeves illustrated in FIG. 26, which are disposed within a plurality of holes defined by the distal end of the guide illustrated in FIG. 1, and a pin illustrated in FIG. 30 disposed within the pin sleeve illustrated in FIG. 29, which is disposed within the hole defined by the proximal end of the guide illustrated in FIG. 1, in accordance with some embodiments.

After all adjustments are made, the angel wing alignment guide 200 and alignment rod 270 are removed. As illustrated in FIGS. 34-35, pin sleeves 144, 146 are inserted into at least one hole 138 of base 116 of the flexion/extension guide 100. A trocar, such as trocar 178 illustrated in FIG. 31, may be inserted into each of the pin sleeves 144, 146 to create "stab wounds" or indentation in the bone to prevent skiving for drilling of percutaneous pins. The trocar 178 is then removed.

As illustrated in FIGS. 34-35, pins 140, 142 are inserted into each of the pin sleeves 144, 146 and through both cortices of the tibia 260, which is used for positioning of other structures of the total ankle replacement system. Once the pins 140, 142 are placed, the pin sleeves 144, 146 are removed and knobs 135, 136 and 137 are loosened to aid in the removal of the flexion/extension guide 100. The guide pin 150 and pin sleeve 152 are then removed, followed by the flexion/extension guide 100, rotation guide slide 20 and gutter fork 10, leaving pins 140, 142 in the tibia 260.

The tibia and talus may be further prepared for ankle replacement surgery with an implant using any suitable surgical technique, including the technique disclosed in U.S. Pat. No. 10,136,904, which was incorporated by reference above.

Although the guides, systems, and methods have been described in terms of exemplary embodiments, they are not limited thereto. Rather, the appended claims should be construed broadly, to include other variants and embodiments of the guides, systems, and methods, which may be made by those skilled in the art without departing from the scope and range of equivalents of the guides, systems, and methods.

What is claimed is:

1. A surgical guide, comprising:

a body having a first side, a second side, a third side, and a fourth side, the third and fourth sides extending between the first and second sides, wherein the body comprises a first base at said first side, a second base at said second side and an elongated extension between the first and second base; wherein the first base defines at least one first hole configured to receive at least one pin and the second base having a superior side and an inferior side; and an engagement portion, disposed within a channel configured to allow movement of the engagement portion between the superior side and inferior side of the second base wherein the engagement portion defines at least a second hole configured to receive at least one pin sleeve and the at least one pin, an adjustment mechanism configured to lock the at least one pin in place, wherein the pin sleeve comprises at least one slot configured to engage a portion of the adjustment mechanism configured to lock a pin in place;

wherein the body is sized and configured to be installed above a joint line of a calcaneus and a talus bone and approximately mid-way along a longitudinal axis of a tibia; and wherein the first base is configured to receive at least one dowel of a second surgical guide in the at least one first hole and the second base is configured to receive at least one pin sleeve and pin in the second hole.

2. The surgical guide of claim 1, wherein the first base includes a posterior side comprising a protrusion configured to engage a channel of a third surgical guide.

3. The surgical guide of claim 2, wherein the first base includes an anterior side comprising an adjustment mechanism to lock the third surgical guide and the surgical guide.

4. The surgical guide of claim 1, wherein the first base includes a posterior side comprising a channel configured to engage a side of a third surgical guide.

5. The surgical guide of claim 4, wherein the first base includes an anterior side comprising an adjustment mechanism to lock the third surgical guide and the surgical guide.

6. The surgical guide of claim 1, wherein the first and second base are rectangular in shape.

7. The surgical guide of claim 1, wherein the second base further comprises an adjustment mechanism to lock the engagement portion in place.

8. The surgical guide of claim 1, wherein the engagement portion is rectangular in shape.

9. The surgical guide of claim 1, wherein the pin sleeve comprises two slots, wherein one slot is located on the superior side of the pin sleeve and one slot is located on the inferior side of the pin sleeve, and wherein each slot is configured to engage a portion of the adjustment mechanism configured to lock a pin in place in either configuration of the pin sleeve.

10. The surgical guide of claim 1, wherein the pin sleeve is rectangular in shape and the second hole is similarly configured to receive the rectangular shape of the pin sleeve.

11. The surgical guide of claim 1, wherein at least a portion of the body is formed from radiopaque material.

12. A system, comprising:

a first guide including:

a body having a first side, a second side, a third side, and a fourth side, the third and fourth sides extending between the first and second sides, wherein the body comprises a first base at said first side, a second base at said second side wherein the second base includes a superior side and an inferior side and an elongated extension between the first and second base, wherein the first base defines at least one first hole and the second base defines at least a second hole;

an engagement portion, disposed within a channel configured to allow movement of the engagement portion between the superior side and inferior side; and an adjustment mechanism to lock the engagement portion in place;

wherein the body is sized and configured to be installed above a joint line of a calcaneus and a talus bone and approximately mid-way along the longitudinal axis of a tibia; and wherein the first base is configured to receive at least one protrusion of a second surgical guide in the at least one first hole and the second base is configured to receive at least one pin sleeve and pin in the second hole, wherein the engagement portion defines at least the second hole configured to receive the at least one pin sleeve and pin, wherein the pin sleeve comprises a slot configured to engage a portion of the adjustment mechanism configured to lock a pin in place.

13. The surgical guide of claim 12, wherein the pin sleeve comprises two slots;

wherein one slot is located on the superior side of the pin sleeve and one slot is located on the inferior side of the pin sleeve; and wherein each slot is configured to engage a portion of the adjustment mechanism configured to lock a pin in place in either configuration of the pin sleeve.

14. The system of claim 12, further comprising:

a second guide, the second guide having a transverse beam that extends between a first arm and a second arm, wherein the second guide is configured to be coupled to the first guide.

15. The system of claim 14, wherein first and second protrusions extend from the transverse beam of the second guide, the first and second protrusions sized and configured to be received in the at least one first hole defined by the first base for coupling the second guide to the first guide.

16. The system of claim 15, wherein each of the first and second arms of the second guide define at least one of a hole or a slot for receiving an elongate radiopaque device therein.

17. The system of claim 15, further comprising:

a third guide, the third guide having a first portion extending longitudinally in a first direction and a second portion extending laterally from the first portion in a second direction, wherein the first portion defines a first channel that runs the length of first portion on a first side and defines a second channel on a second side, which is disposed opposite the first side.

18. The system of claim 17, wherein the second portion of the third guide defines a guide hole which is configured to engage a shaft of a fourth surgical guide inserted above a joint line of a calcaneus and a talus bone.

19. The system of claim 17, wherein the first base includes a posterior side comprising a protrusion configured to engage a channel of the third guide.

20. The surgical guide of claim 17, wherein the first base includes a posterior side comprising a channel configured to engage a side of the third surgical guide.

21. The system of claim 17, wherein the first base includes an anterior side comprising an adjustment mechanism to align the third guide and the first guide.

* * * * *